United States Patent
Erdmann et al.

(10) Patent No.: US 10,426,639 B2
(45) Date of Patent: Oct. 1, 2019

(54) MULTI-CHAMBER VACUUM PUMP

(71) Applicant: Otto Bock HealthCare LP, Austin, TX (US)

(72) Inventors: John A. Erdmann, Holladay, UT (US); Charles C. Polta, Gottingen (DE); Florian W. S. Poser, Salt Lake City, UT (US); Douglas E. Rush, Salt Lake City, UT (US)

(73) Assignee: Otto Bock HealthCare LP, Austin, TX (US)

( * ) Notice: Subject to any disclaimer, the term of this patent is extended or adjusted under 35 U.S.C. 154(b) by 148 days.

(21) Appl. No.: 15/253,582

(22) Filed: Aug. 31, 2016

(65) Prior Publication Data

US 2018/0055661 A1    Mar. 1, 2018

(51) Int. Cl.
*A61F 2/80* (2006.01)
*A61F 2/66* (2006.01)
*A61F 2/68* (2006.01)

(52) U.S. Cl.
CPC .............. *A61F 2/80* (2013.01); *A61F 2/66* (2013.01); *A61F 2/68* (2013.01); *A61F 2002/6614* (2013.01); *A61F 2002/802* (2013.01); *A61F 2002/805* (2013.01); *A61F 2002/807* (2013.01)

(58) Field of Classification Search
CPC .............. A61F 2/80; A61F 2002/802; A61F 2002/805; A61F 2002/807
See application file for complete search history.

(56) References Cited

U.S. PATENT DOCUMENTS

| | | |
|---|---|---|
| 6,554,868 B1 | 4/2003 | Caspers |
| 6,645,253 B2 | 11/2003 | Caspers |
| 6,761,742 B2 | 7/2004 | Caspers |
| 6,827,343 B2 | 12/2004 | Skiera |
| 7,025,792 B2 | 4/2006 | Collier |
| 7,744,653 B2 | 6/2010 | Rush et al. |
| 8,568,489 B2 | 10/2013 | Finlinson et al. |
| 8,951,304 B2 | 2/2015 | Wu et al. |
| 2009/0036998 A1* | 2/2009 | Finlinson ............... A61F 2/78 623/34 |
| 2012/0123559 A1 | 5/2012 | Mosler et al. |

(Continued)

FOREIGN PATENT DOCUMENTS

| | | |
|---|---|---|
| WO | 01/70147 A2 | 9/2001 |
| WO | 02/067825 A2 | 9/2002 |

OTHER PUBLICATIONS

Partial European Search Report for EP Application No. 17186884.7, dated Feb. 12, 2018 (13 pp.).

*Primary Examiner* — Bruce E Snow
(74) *Attorney, Agent, or Firm* — Holland & Hart, LLP

(57) ABSTRACT

A vacuum pump may be used to attach a prosthetic and/or orthotic device to a residual limb. The vacuum pump may be in line below a socket of a residual limb. The socket may be a portion of the prosthesis that accepts the residual limb. The vacuum pump may generate a vacuum condition between the prosthesis and the residual limb. Generally, a vacuum condition may be generated between a socket and the residual limb. The residual limb may be covered with a sock, elastomeric liner, or sheath covering the limb. The vacuum condition may positively attach the prosthesis to the residual limb without the need for straps, retaining pins, or suction type vacuum which do not use a vacuum pump.

22 Claims, 22 Drawing Sheets

(56) References Cited

U.S. PATENT DOCUMENTS

| | | |
|---|---|---|
| 2012/0173000 A1 | 7/2012 | Caspers |
| 2012/0173001 A1 | 7/2012 | Caspers |
| 2013/0096694 A1 | 4/2013 | Caldwell et al. |
| 2013/0150980 A1 | 6/2013 | Swift et al. |
| 2013/0211544 A1 | 8/2013 | Jonsson et al. |
| 2013/0289741 A1 | 10/2013 | Halldorsson et al. |
| 2013/0289742 A1 | 10/2013 | Halldorsson et al. |

\* cited by examiner

MULTI-CHAMBER VACUUM PUMP

TECHNICAL FIELD

The present disclosure relates generally to prosthetic systems and methods, and relates particularly to systems and methods for generating a vacuum condition that assists in connecting a prosthetic device to a residual limb.

BACKGROUND

An amputee is a person who has lost part of an extremity or limb such as a leg or arm. The extremity of the limb left after amputation is termed a residual limb or a stump. Residual limbs come in various sizes and shapes depending on the person and the amputation. New amputations may be slightly bulbous or cylindrical in shape. Older amputations may have atrophied and may become more conical shape. A residual limb may additionally or alternatively be characterized by various individual problems and configurations including the volume and shape of the stump and possible scar, skin graft, bony prominence, uneven limb volume, neuroma, pain, edema or other soft tissue configurations. Prosthetic and orthotic devices may provide enhanced mobility and/or functionality to amputees but must be secured to a residual limb to do so. Keeping and maintaining a strong connection between a residual limb and a prosthetic or orthotic device is difficult.

There is, therefore, a need for improvements in how prosthetic and orthotic devices are connected to an maintain connection with the residual limb of an amputee.

SUMMARY

A vacuum pump may be used to attach a prosthetic device to a residual limb. The vacuum pump may be positioned in line and distal to a socket of the prosthetic device. The socket may be a portion of the prosthesis that accepts the residual limb. The vacuum pump may generate a vacuum condition that is applied in the socket to maintain a connection between the prosthetic device and the residual limb. The residual limb may be covered with a sock, elastomeric liner, or sheath covering the limb. The covered residual limb may be inserted into socket of the prosthetic device. The vacuum condition provided by the vacuum pump may positively attach the prosthesis to the residual limb using very low pressure and without the need for straps, retaining pins, or other types of suction devices that do not use a vacuum pump.

According to one aspect of the present disclosure, a vacuum pump for a prosthesis is described. The vacuum pump includes a housing having an inner wall. The vacuum pump also includes a piston having an outer diameter and the piston is secured within the housing. A shaft having an inner surface is positioned between the inner wall of the housing and the outer diameter of the piston. An upper fluid chamber is positioned between a top surface of the piston and the inner surface of the shaft. The upper chamber has a variable volume as the shaft moves axially in relation to the piston and the housing. The upper chamber is fluidly connected to a socket of the prosthesis through a first valve and is fluidly connected to atmosphere through a second valve. A lower fluid chamber is positioned between a bottom surface of the piston and the inner surface of the shaft. The lower fluid chamber has a variable volume as the shaft moves axially in relation to the piston and the housing. The lower fluid chamber is fluidly connected to the socket through a third valve and is fluidly connected to atmosphere through a fourth valve.

In some embodiments, the first valve and third valve may be independently fluidly connectable to an evacuation volume. In some instances, the evacuation volume may decrease as the vacuum pump operates, thereby causing a vacuum condition in the evacuation volume. The shaft may be axially movable to compress a volume of the upper fluid chamber while expanding a volume of the lower fluid chamber and vice versa. In some embodiments, compressing a volume of the upper fluid chamber may cause air to exhaust via the second valve into atmosphere.

In some instances, the piston may be an assembly comprising a first piece of the piston, wherein the first piece of the piston is substantially cylindrically shaped. A second piece of the piston may be a flattened torus. The second piece of the piston and first piece of the piston may form the piston assembly. In some embodiments, the first piece of the piston may incorporate a series of fluid channels fluidly connecting the upper chamber and the lower chamber to the socket.

In some instances, a compressible seal may be positioned around an outer diameter of the piston. In some embodiments, the compressible seal may fluidly separate the upper chamber from the lower chamber while enabling the shaft to move axially in relation to the piston. In some instances, the valves are one-way valves allowing fluid flow in a single direction. The vacuum pump may also comprise a prosthetic leg, wherein the prosthetic leg comprises a prosthetic foot and a socket, with the socket being configured to accept a residual limb and the vacuum pump being configured to evacuate fluid from the socket.

In another aspect of the disclosure, a vacuum pump for a prosthetic device is provided which may comprise a housing having an inner wall, a piston having an outer diameter and being secured within the housing, and a shaft having an inner surface and being positioned between the inner wall of the housing and the outer diameter of the piston. An upper fluid chamber may be positioned between a top surface of the piston and the inner surface of the shaft, wherein the upper fluid chamber may have a variable volume as the shaft moves axially in relation to the piston and the housing. The upper fluid chamber may also be fluidly connected to a first pair of one-way valves. A lower fluid chamber may be positioned between a bottom surface of the piston and the inner surface of the shaft, wherein the lower fluid chamber may have a variable volume as the shaft moves axially in relation to the piston and the housing. The lower fluid chamber may be fluidly connected to a second pair of one-way valves.

In some arrangements, at least a first valve of the first and second pair of one-way valves may be fluidly connected to a socket of the prosthetic device, and at least a second valve of the first and second pair of one-way valves may be fluidly connected to atmosphere. Compressing a volume of the upper fluid chamber may cause air to exhaust via the one of the first pair of one-way valves into atmosphere.

The pump may also comprise a compressible seal positioned around an outer diameter of the piston, wherein the compressible seal fluidly separates the upper fluid chamber from the lower fluid chamber while enabling the shaft to move axially in relation to the piston.

Yet another aspect of the disclosure relates to a vacuum pump for a prosthetic device, wherein the vacuum pump comprises a shaft, a housing, a first fluid chamber, a second fluid chamber, and a third fluid chamber. Each of the first, second, and third fluid chambers may be sealed and may have a variable volume upon movement of the shaft relative to the housing. The first fluid chamber may be fluidly connected to a first pair of one-way valves, the second fluid chamber may be fluidly connected to a second pair of one-way valves, and the third fluid chamber may be fluidly connected to a third pair of one-way valves.

At least one of the one-way valves may be shared by the first pair of one-way valves and the second pair of one-way valves. The first and second fluid chambers may be arranged in series or in parallel.

Still another aspect of the disclosure relates to a vacuum pump for a prosthetic device that may comprise a housing having an inner wall, a piston having an outer diameter, a top surface, and a bottom surface, with the piston being held stationary relative to the housing, and a shaft having an inner surface and being positioned between the inner wall of the housing and the outer diameter of the piston. An upper fluid chamber may be positioned between the top surface of the piston and the inner surface of the shaft, wherein the upper fluid chamber may have a variable volume as the shaft moves axially in relation to the piston and the housing and the upper fluid chamber may be in fluid communication with a first valve and a second valve. A lower fluid chamber may be positioned between the bottom surface of the piston and the inner surface of the shaft, wherein the lower fluid chamber may have a variable volume as the shaft moves axially in relation to the piston and the housing and the lower fluid chamber may be in fluid communication with a third valve and a fourth valve. A switch may be configured to control the operation of the vacuum pump between a parallel vacuum pump configuration and a series vacuum pump configuration, and at least one of the first and third valves may be fluidly connected to the a socket of the prosthetic device and at least one of the second and forth valve may be fluidly connected to atmosphere.

In some embodiments, when the vacuum pump is in the parallel vacuum pump configuration, the first and third valves are both fluidly connected to the socket and the second and fourth valves are fluidly connected to atmosphere. When the vacuum pump is in the series vacuum pump configuration, the first valve may be fluidly connected to the socket, the second valve may be fluidly connected to the lower fluid chamber, the third valve may be fluidly connected to the lower fluid chamber, and the fourth valve may be fluidly connected to atmosphere.

A further aspect of the present disclosure relates to a method of operating a vacuum pump for a prosthetic device. The method includes providing a vacuum pump. The vacuum pump includes a housing having an inner wall, and a piston having an outer diameter and being secured within the housing. The vacuum pump includes a shaft having an inner surface. The shaft is positioned between the inner wall of the housing and the outer diameter of the piston. The vacuum pump includes an upper fluid chamber positioned between a top surface of the piston and the inner surface of the shaft. The upper chamber has a variable volume as the shaft moves axially in relation to the piston and the housing. The upper chamber is fluidly connected to a socket of the prosthesis through a first valve and fluidly connected to atmosphere through a second valve. A lower fluid chamber is positioned between a bottom surface of the piston and the inner surface of the shaft. The lower chamber has a variable volume as the shaft moves axially in relation to the piston and the housing. The lower fluid chamber is fluidly connected to the socket through a third valve and fluidly connected to atmosphere through a fourth valve. The method includes attaching the vacuum pump to the socket. The socket is configured to receive a residual limb that has a liner mounted thereto. The method includes moving the shaft in a first axial direction relative to the piston thereby causing air to exhaust from the first chamber through the second valve and air to be drawn into the second chamber through the third valve. The method further includes moving the shaft in a second axial direction relative to the piston thereby causing air to exhaust from the second chamber through the fourth valve and air to be drawn into the first chamber through the first valve.

In some embodiments, the method may include generating a vacuum condition between the socket and the liner when air is drawn into the second chamber through the third valve.

In some instances, the method may include connecting the pump to a prosthetic foot and transferring load from the socket to the foot through the pump.

In some instances, the method may include increasing a fluid volume of the second chamber as the shaft moves axially in the first direction. The method may include decreasing a fluid volume of the first chamber as the shaft moves axially in the first direction. In some embodiments, the method may include increasing a fluid volume of the second chamber as the shaft moves axially in the first direction. The method may include decreasing a fluid volume of the first chamber as the shaft moves axially in the first direction.

Another aspect of the disclosure relates to a vacuum pump switch for a prosthetic device, wherein the switch may comprise a housing, an inlet passage formed in the housing and configured to provide fluid communication with an evacuation volume, a first fluid inlet valve passage configured to provide fluid communication to a first chamber of a vacuum pump, a second fluid inlet valve passage configured to provide fluid communication to a second chamber of the vacuum pump, a first fluid outlet valve passage configured to provide fluid communication to the first chamber, a second fluid outlet valve passage configured to provide fluid communication to the second chamber, an outlet passage formed in the housing, and a switch. The switch may be operable between a first position and a second position. In the first position, fluid flow from the inlet passage may be provided simultaneously to the first and second fluid inlet valve passages and flow to the outlet passage may be provided simultaneously from the first and second fluid outlet valve passages. In the second position, fluid flow from the inlet passage may be provided to the first fluid inlet valve passage, fluid flow to the second fluid inlet valve passage may be provided from the first fluid outlet valve passage, and fluid flow to the outlet passage may be provided from the second fluid outlet valve passage.

In some arrangements, the vacuum pump switch may also comprise a vacuum pump comprising a housing and a piston, with the housing comprising a sealed volume and with the piston dividing the sealed volume into the first chamber and the second chamber.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein-including their organization and method of operation-together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1:
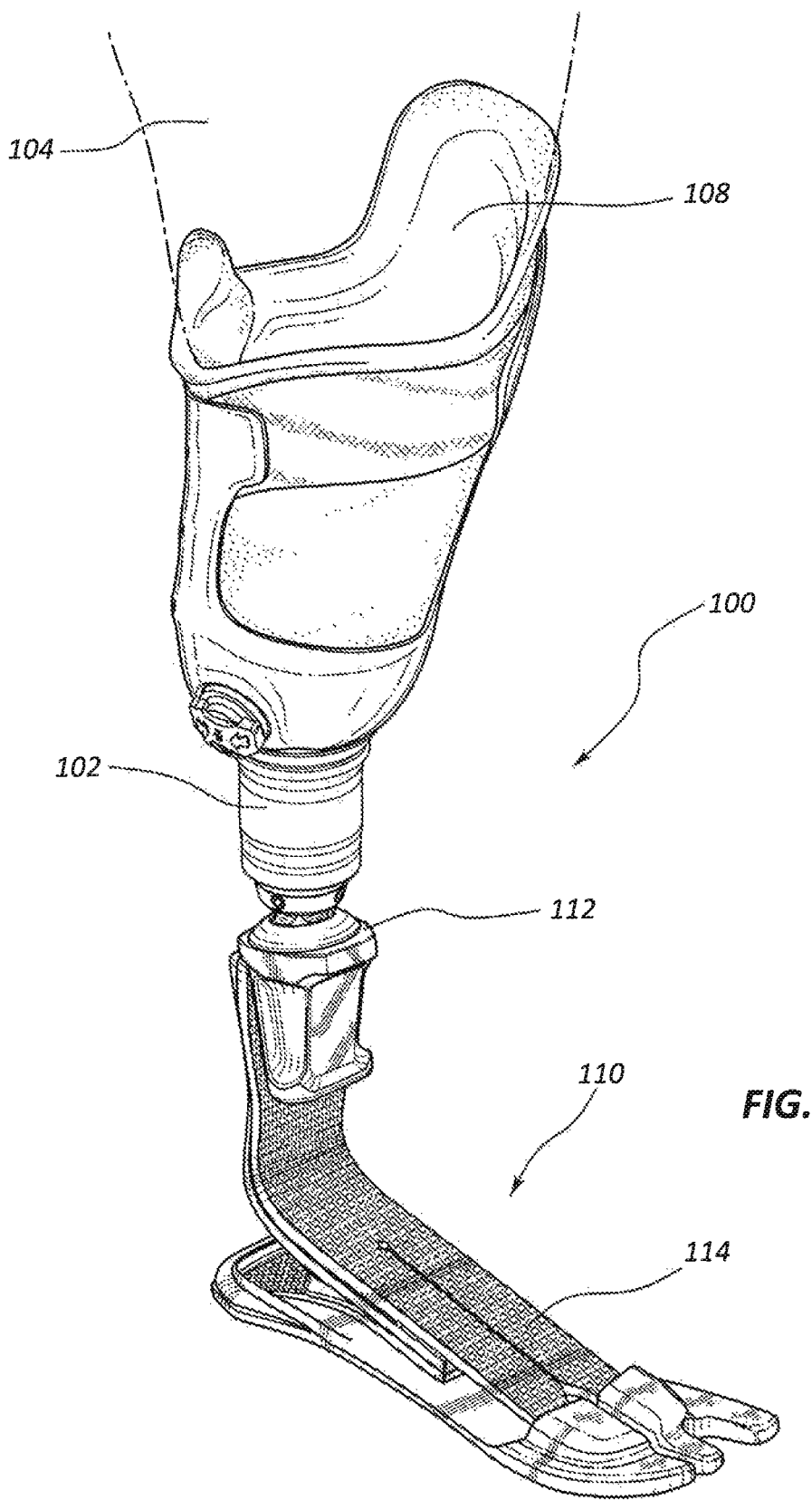
FIG. 1 illustrates an example prosthetic device coupled to a residual limb using a vacuum pump in accordance with the present disclosure.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

Vacuum suspension may be used to couple a prosthetic device (also referred to as a prosthesis) to a residual limb. When a limb interface is subject to high levels of vacuum, retention may occur with no significant movement between the residual limb and the prosthetic device. The vacuum condition may additionally provide residual limb volume management and increased proprioception. Vacuum suspension may additionally improve circulation and may increase a rate at which a wound heals on the residual limb.

Vacuum level is the difference in air pressure between an evacuated volume and a neighboring volume. The neighboring volume in a prosthetic application may be atmospheric pressure. Initially, a socket of the prosthetic device does not have adequate vacuum suspension to realize its benefits. To initiate vacuum suspension, a vacuum pump may be cycled after a prosthetic device is attached to a residual limb. The cycling of the vacuum pump may generate a vacuum suspension which may enable the benefits aforementioned. Cycling a vacuum pump, as mentioned herein, is running a vacuum cycle several times. Additional layers of material may be located between the socket and liner to facilitate fit, comfort, and/or the evacuation of air.

During use, the vacuum volume may leak and the vacuum condition may bleed off if the vacuum pump is not cycled. This may occur during periods of inactivity of the pump. If the pump is a mechanical pump, this may equate to inactivity of a user. Prior to a person then using a prosthetic attached with a vacuum interface, an adequate vacuum suspension condition may need to be achieved. Quickly achieving the vacuum suspension may enable an amputee to become mobile more quickly.

FIG. 1 is an example use of a prosthesis 100 with a vacuum pump 102. The prosthesis 100 may attach to a residual limb 104. The residual limb 104 may fit into a liner or sock (not shown) (or the liner or sock may be donned on or mounted to the residual limb 104). The residual limb 104 with liner mounted thereto may then be inserted into a socket 108. In some embodiments, additional layers of material may be located between the socket and liner to facilitate fit, comfort, and/or the evacuation of air between the socket and liner. The socket 108 may be fluidly connected to the vacuum pump 102. The socket 108 may be rigidly coupled to other components of the prosthesis, such as prosthetic 110. The prosthetic 110 may include a prosthetic shaft 112 and a prosthetic foot 114.

The vacuum pump 102 may be an electrical or mechanical pump. A mechanical pump, as will be discussed, is cycled mechanically by the user's weight during use to generate a vacuum pressure condition (also referred to as a vacuum force or a vacuum condition). An electrical pump requires a power source (not shown) to energize the pump and create a vacuum. The power source may comprise a battery. The battery may be replaceable and/or rechargeable. In some embodiments, use of the prosthesis 100 may generate a charge for the power source.

Figure 2A:
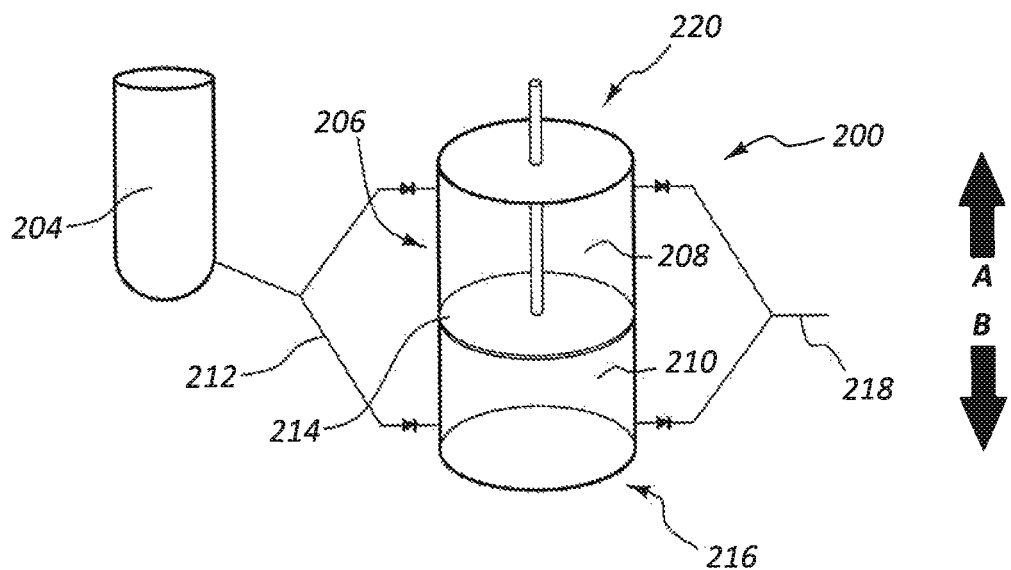
FIG. 2A is a schematic representation of a parallel multi-chamber vacuum pump.
Figure 2B:
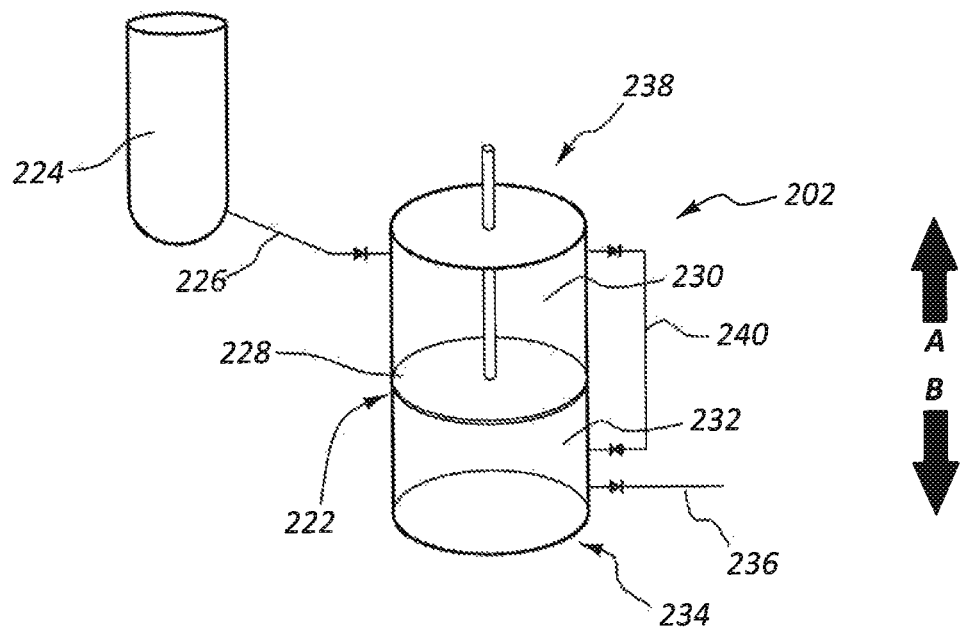
FIG. 2B is a schematic representation of a series multi-chamber vacuum pump.

As shown in FIGS. 2A and 2B, the vacuum pump 102 may be a parallel vacuum pump 200 (see FIG. 2A) or a series vacuum pump 202 (see FIG. 2B). A parallel vacuum pump 200 includes two or more pumping chambers 208, 210 and is configured to draw air out of a single volume to be evacuated (e.g., the socket 108 or a chamber that is in fluid communication with socket 108). A series vacuum pump 202 includes a pumping chamber 230 that is connected to the volume to be evacuated and exhausts to a second chamber 232.

As shown in FIG. 2A, a parallel vacuum pump 200 is fluidly connected to an evacuation volume 204. The parallel vacuum pump 200 includes closed, sealed volume 206 comprising a first chamber 208 and a second chamber 210. The first chamber 208 and second chamber 210 are fluidly connected to the evacuation volume 204 via one or more intake passages 212. A piston 214 moves within the sealed volume 206 and defines in part the first and second chambers 208, 210 within the sealed volume 206. The piston 214 may define a wall, that, in some embodiments, moves axially in the direction A-B relative to other components of the parallel vacuum pump 200. The parallel vacuum pump 200 may exhaust a fluid (e.g., air) from the evacuation volume 204 faster than (e.g., two times faster than) a single chamber vacuum pump.

As the piston 214 travels toward a bottom 216 of the sealed volume 206, the piston 214 causes the second chamber 210 to decrease in volume. As the piston 214 moves and the second chamber 210 decreases, the fluid in the second chamber 210 exhausts to atmosphere via one or more exhaust passages 218. At the same time, a volume of the first chamber 208 increases. As the volume of the first chamber 208 increases, it pulls fluid (e.g., air) from the evacuation volume 204 via the one or more intake passages 212. As the piston 214 continues to cycle and move toward a top 220 of the parallel vacuum pump 200, the process switches for the first and second chambers 208, 210. The first chamber 208 reduces in volume and exhausts a fluid via the one or more exhaust passages 218. The second chamber 210 increases in volume and pulls a fluid from the evacuation volume 204 via the one or more intake passages 212. As the piston 214 continues to cycle, fluid continues to be pulled from the evacuation volume 204 thereby creating a vacuum condition in the evacuation volume 204.

FIG. 2B displays an schematic of the series vacuum pump 202. The series vacuum pump 202 may comprise a closed, sealed volume 222, which may be fluidly connected to an evacuation volume 224 via one or more intake passages 226. A piston 228 may separate the sealed volume 222 into two chambers; a first chamber 230 and a second chamber 232. The one or more intake passages 226 fluidly connects the evacuation volume 224 to the first chamber 230 of the series vacuum pump 202.

As the piston 228 moves towards a bottom 234 of the series vacuum pump 202, the first chamber 230 may pull a fluid from the evacuation volume 224 via the one or more intake passages 226. At the same time, a volume of the second chamber 232 reduces. As the volume of the second chamber 232 reduces, the fluid in the second chamber 232 exits the chamber 232 via one or more exhaust passages 236. The one or more exhaust passages 236 fluidly connects the second chamber 232 to either a third chamber (not shown) or atmosphere. As the piston 228 reciprocates and moves toward a top 238 of the series vacuum pump 202, the volume of the first chamber 230 is reduced and the volume of the second chamber 232 is increased. This causes the fluid in the first chamber 230 to exhaust and enter the second chamber 232 via connection passage 240.

This process then continues and the piston 228 reciprocates back toward the bottom 234 of the series vacuum pump 202. This process creates a vacuum condition that may result in a higher differential pressure, or increased vacuum, that may be applied to a space between the residual limb/liner and the socket.

Figure 3A:
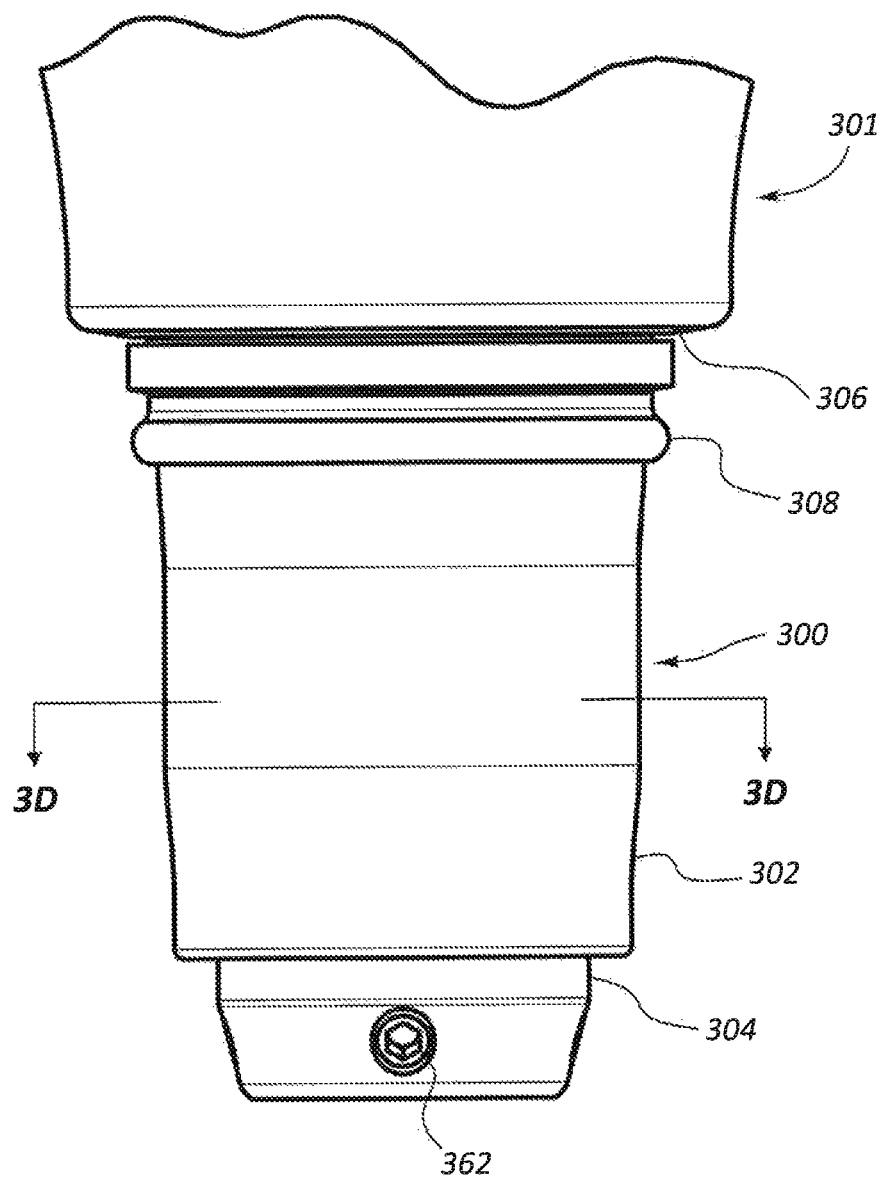
FIG. 3A is a side view of an example vacuum pump in accordance with the present disclosure.
Figure 3B:
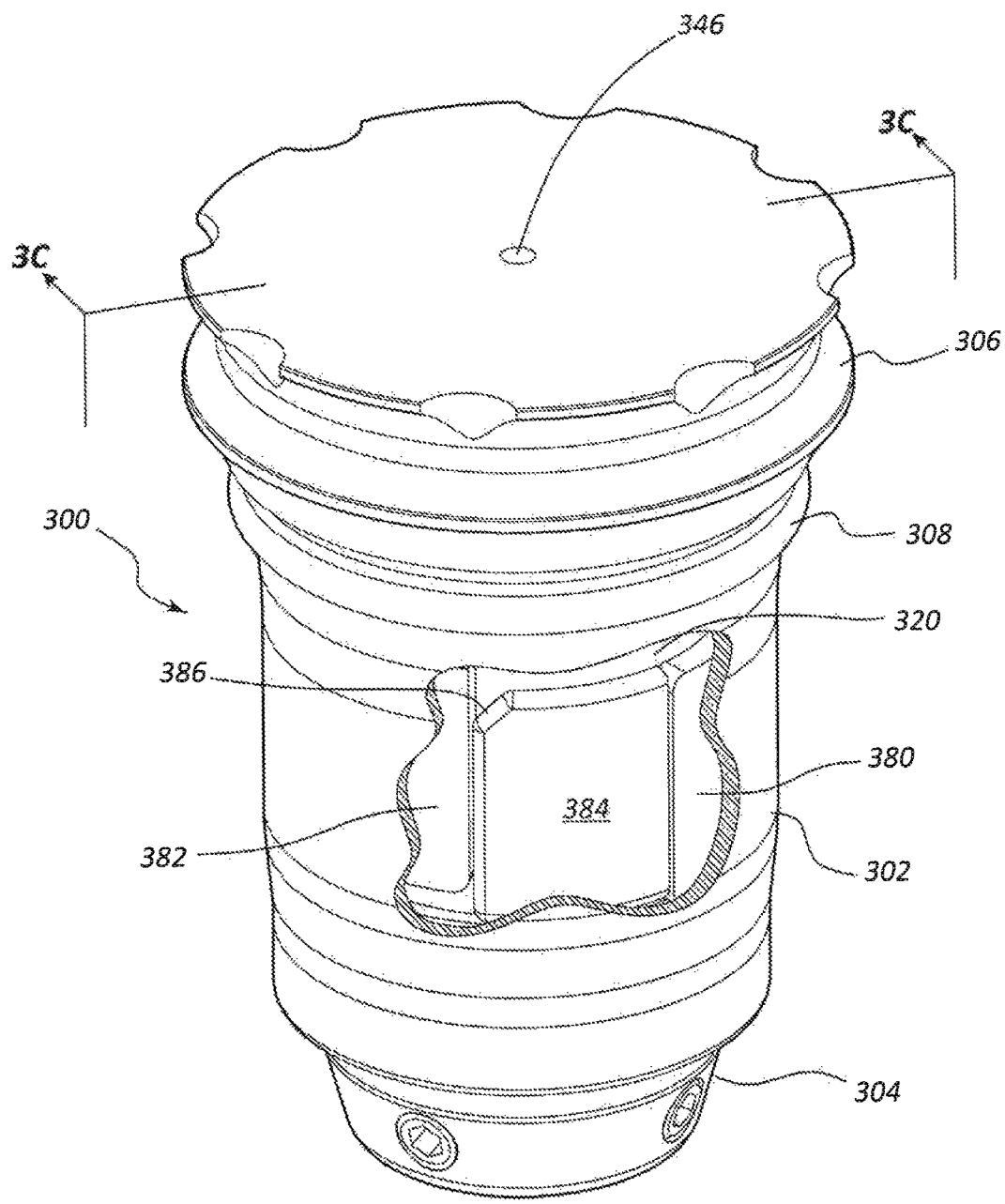
FIG. 3B is a perspective view of the vacuum pump shown in FIG. 3A with a cutaway side portion showing internal components.
Figure 3C:
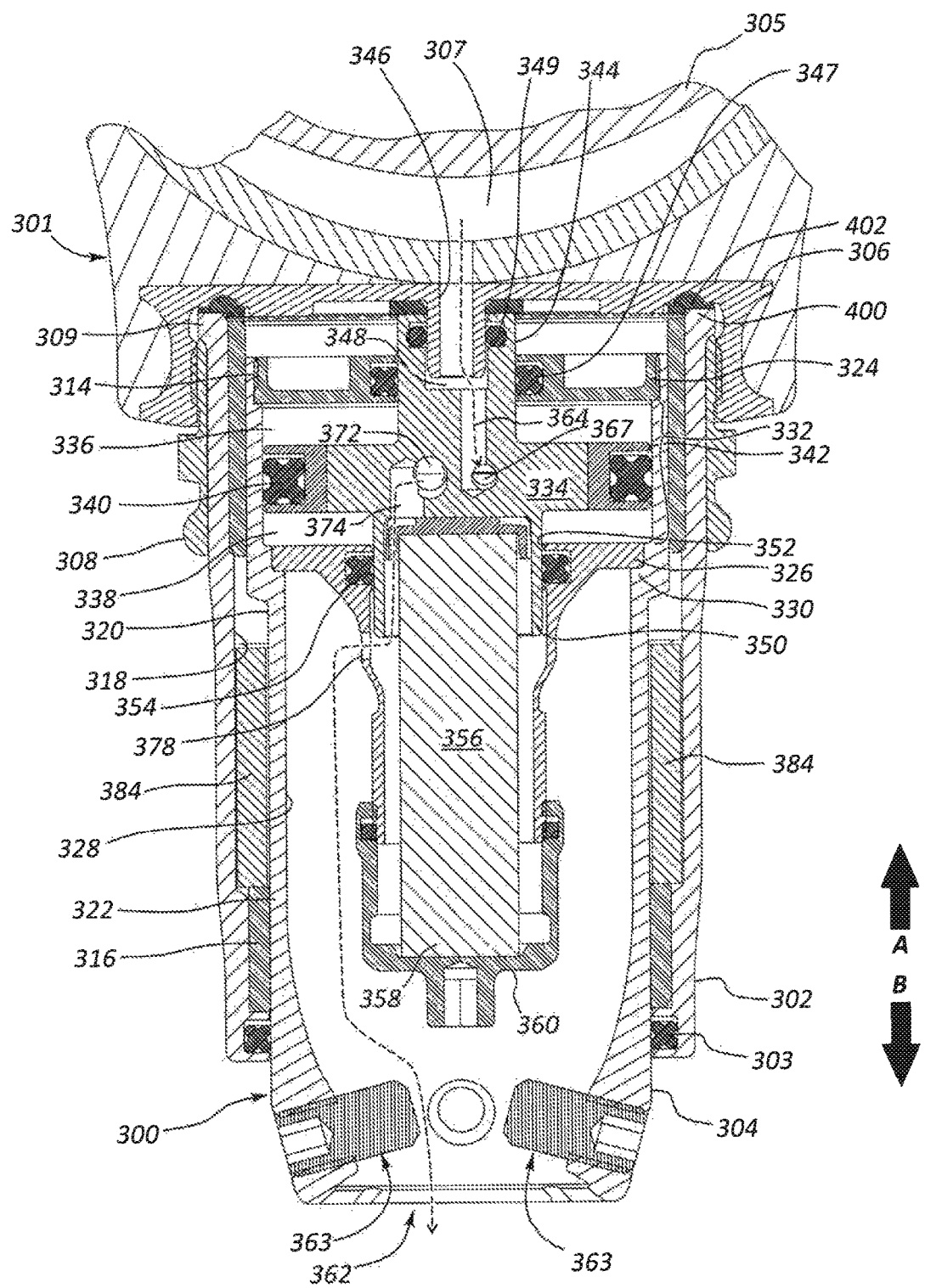
FIG. 3C is a cross-sectional side view of the vacuum pump shown in FIG. 3A taken along cross-section indicators 3C-3C shown in FIG. 3B.
Figure 3D:
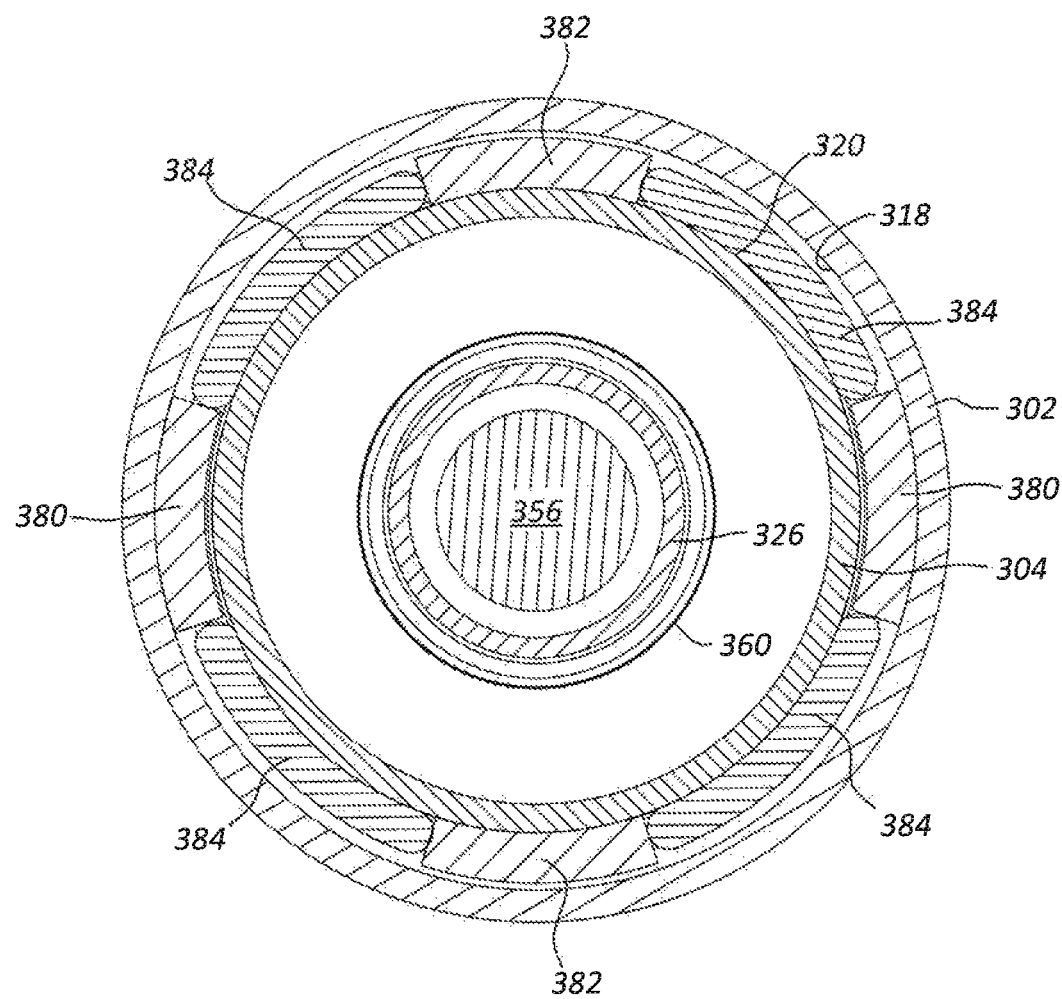
FIG. 3D is a cross-sectional top view of the vacuum pump shown in FIG. 3A taken along cross-section indicators 3D-3D shown in FIG. 3A.
Figure 4:
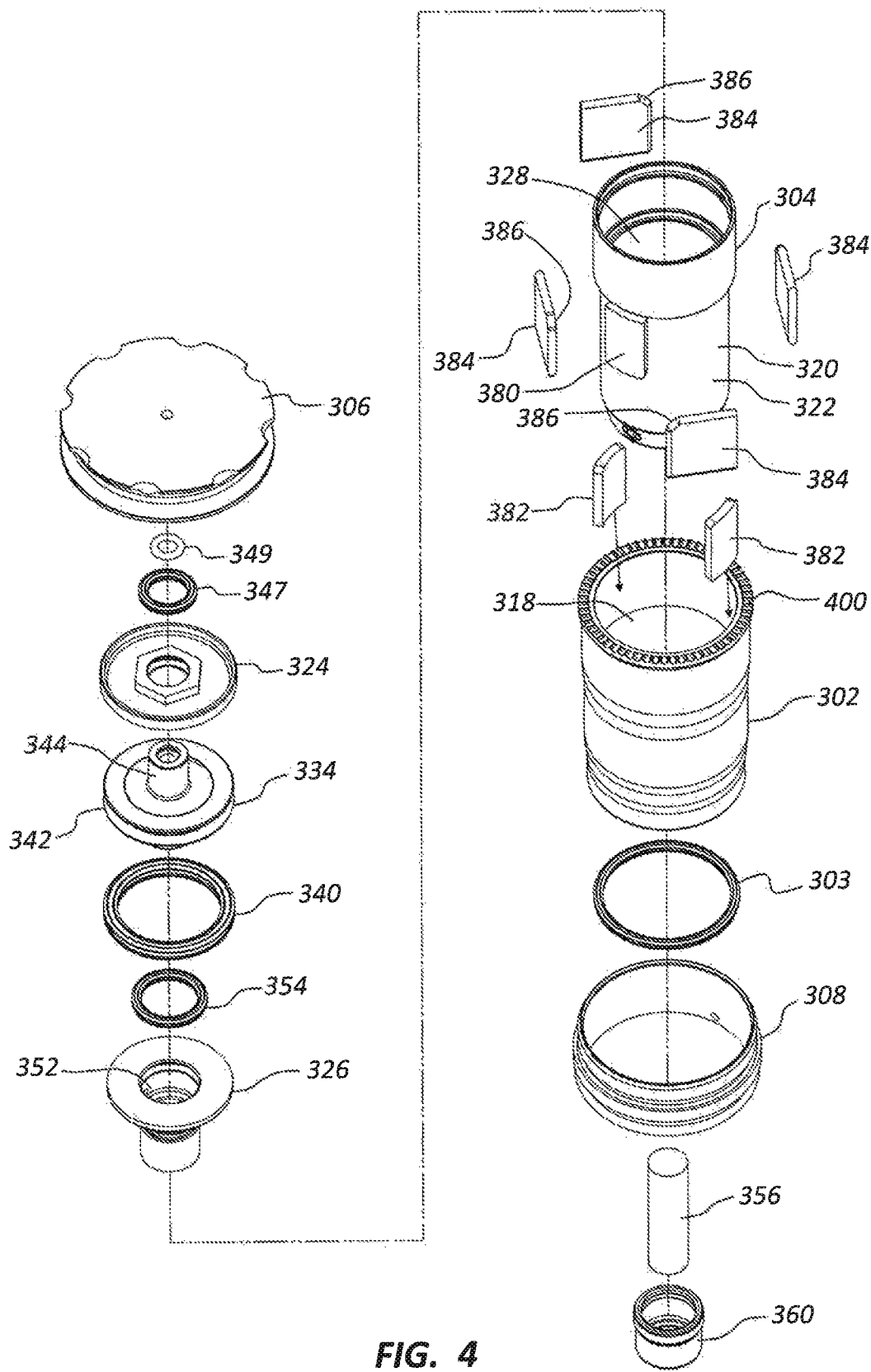
FIG. 4 is an exploded view of the vacuum pump shown in FIG. 3A.

FIGS. 3A-4 show views of an example vacuum pump 300 according to the present disclosure. FIG. 3A is a side view of a vacuum pump 300 connected to a socket 301, FIG. 3B is a perspective view of the vacuum pump 300, FIG. 3C is a side section view of the vacuum pump 300 and socket 301 taken through section lines 3C-3C in FIG. 3B, FIG. 3D is a top section view of the vacuum pump 300 taken through section lines 3D-3D in FIG. 3A, and FIG. 4 is an exploded view of the vacuum pump 300. The vacuum pump 300 may be a parallel pump.

The vacuum pump 300 in FIG. 3C comprises a housing 302 and a shaft 304. The shaft 304 may move in relation to the housing 302. A cap 306 may be coupled to the housing 302. The cap 306 may alternatively be referred to as a lamination plate because it may be laminated to a limb socket 301. The housing 302 and cap 302 may be connected to each other using a threaded member 308. The cap 306 may threadably engage the threaded member 308 to couple to the housing 302. A lip 309 at the top of the housing 302 may keep the housing 302 from sliding out of the threaded member 308. The housing 302 and cap 306 may alternatively be clamped together via mating threads, fastened together, adhered together, or otherwise coupled. Teeth 400, 402 may be positioned on the housing 302 and cap 306, respectively, to help prevent the housing 302 from rotating relative to the cap 306 once the threaded member 308 is tightened against the threads of the cap 306. See also FIG. 4 and related descriptions below.

The radial outer surface of the cap 306 may be laminated or otherwise affixed and attached to a limb socket 301 within which a limb liner 305 may be positioned. Thus, the cap 306 may be formed integrally with the socket 301. An evacuation volume 307 may be formed between the outer surface of the limb liner 305 and the inner surface of the socket 301. The cap 306 may additionally comprise an air passage 310 in fluid communication with the evacuation volume 307. The evacuation volume 307 may be a volume from which air is drawn by the pump 300, such as evacuation volume 204.

A first bearing 314 and a second bearing 316 may provide a smooth, sliding interface between the housing 302 and the shaft 304. The first bearing 314 and second bearing 316 may provide support between the shaft 304 and housing 302 as the shaft 304 and the housing 302 move in relation to each other. The bearings 314, 316 may also maintain a working distance between an inner wall 318 of the housing 302 and an outer wall 320 of the shaft 304. A bottom seal 303 may keep out dirt and other contaminants from entering the interface between the housing 302 and shaft 304.

The shaft 304 may comprise a multi-piece assembly. See FIGS. 3C and 4. For example, the shaft 304 may be an assembly comprising a body 322, a top cap 324, and a bottom cap 326. The bottom cap 326 may be coupled to an internal wall 328 of the body 322. The bottom cap 326 may be tight-fit, press-fit, screwed, adhered, or otherwise coupled to the body 322. In some embodiments, the bottom cap 326 may rest on a lip 330 on the internal wall 328 of the body 322. The top cap 324 is coupled to a top of the body 322 of the shaft 304. The top cap 324, bottom cap 326, and body 322 may form a sealed volume 332. The sealed volume 332 may be similar to the sealed volume 206 of the parallel pump 200.

A piston 334 may be situated in the sealed volume 332 and may separate the sealed volume 332 into two evacuation chambers 336, 338. The piston 334 may be movable relative to the sealed volume 332 and may fluidly separate the sealed volume 332 into a first evacuation chamber 336 above the piston 334 and a second evacuation chamber 338 below the piston 334. A compressible seal 340 may be located on an outer diameter 342 of the piston 334 that may fluidly separate the first evacuation chamber 336 and the second evacuation chamber 338 while enabling the piston 334 to reciprocate relative to the shaft 304 within the sealed volume 332.

The piston 334 may engage and contact the underside of the cap 306. In some embodiments, the piston 334 may be attached or affixed to the cap 306. For example, the piston 334 may be threadably engaged with, adhered to, or forced against the cap 306 at a top portion 344 of the piston 334. The top portion 344 of the piston 334 may receive a cylindrical stem 346 of the cap 306 within a hollow portion 348 at the top portion 344. An upper compressible seal 349 and lower compressible seal 347 may maintain the sealed volume 332 while enabling the top portion 344 of the piston 334 to mate with the cylindrical stem 346 of the cap 306 and pass through and move relative to the top cap 324.

A bottom portion 350 of the piston 334 may pass through an opening 352 in the bottom cap 326. The opening 352 may incorporate a compressible seal 354, which may maintain the sealed volume 332 while enabling the bottom portion 350 of the piston 334 to pass through and move relative to the opening 352. The bottom portion 350 of the piston 334 may contact and engage a compressible cylinder 356. The compressible cylinder 356 may be a spring element and may comprise a resilient rod, spring coil, or similar elastically longitudinally compressible member. The compressible cylinder 356 may be fairly rigid, but may act as a spring or dampening feature for the pump 300. The compressible cylinder 356 may have a spring rate within a range of about 10 N/mm to about 350 N/mm. A bottom 358 of the compressible cylinder 356 may contact or be coupled to a bottom cup 360 on the bottom cap 326.

The bottom cup 360 may support the compressible cylinder 356 and allow adjustment of the preload applied to the compressible cylinder 356. A prosthetic pyramid connector may attach to the distal end of the shaft 332 through the opening 362 and be secured using fasteners 363. Alternatively, the distal end of the shaft may be configured to clamp a 30 mm or 34 mm tube (not shown). Thus, the prosthetic shaft and the vacuum pump 300 may be easily separable. For example, a user may utilize different prosthesis components depending on, for example, the type or level of activity the user is engaged in. Alternatively, ease of separation may enable ease of maintenance and care for the vacuum pump 300. Removal of the prosthetic shaft from opening 362 may also allow the user to access the bottom cup 360 to remove, adjust, or service the compressible cylinder 356.

The piston 334, housing 302, cap 306, and socket 301 may be stationary relative to each other and may move in unison/as an assembly relative to the shaft 304 and the top and bottom caps 324, 326. As the piston 334 moves relative to the sealed volume 332, the respective volumes of the first evacuation chamber 336 and the second evacuation chamber 338 may vary. As the piston 334 moves in a direction A relative to the sealed volume 332, the volume of the first evacuation chamber 336 may be reduced and the volume of the second evacuation chamber 336 may be increased. As the piston 334 reciprocates and moves in a direction B relative to the sealed volume 332, the volumes of the first evacuation chamber 336 and second evacuation chamber 338 again change. The volume of the first evacuation chamber 336 may increase and the volume of the second evacuation chamber 338 may decrease. In one embodiment, the piston 334 may be powered by an electrical motor (not shown). In another embodiment, if the prosthesis is a prosthetic leg, the piston 334 may move down in the direction B relative to the sealed volume 332 when a person puts weight on the prosthetic shaft or socket 301 since the weight applies a force to the shaft 304 that drives the shaft upward in direction A relative to the housing 302 and piston 334. When the person takes a step and the weight is released, the piston 334 may move upward in the direction A relative to the sealed volume 332 as the shaft 304 moves downward in direction B relative to the housing 302.

Whether a vacuum pump of the present disclosure operates as a parallel vacuum pump or a series vacuum pump depends upon various fluid passages and connections in the vacuum pump and the socket or evacuation volume. In FIGS. 3A-5D, the vacuum pump 300 is a parallel pump, meaning both the first and second evacuation chambers 336, 338 intake fluid from the evacuation volume 307. Each evacuation chamber 336, 338 may be supplied with air using one-way valves. The one-way valves may enable fluid to flow in a single direction through the valve. Separate one-way valves may permit flow out of the evacuation chambers 336, 338 and into the atmosphere surrounding the vacuum pump 300.

FIGS. 3C and 5B-5E illustrate air passages and chambers used to evacuate the evacuation volume 307. Various views of the same piston 334 are shown in FIGS. 3C and 5A-5E. A first vertical intake passage 364 fluidly connects the evacuation volume 307 with the inside of the piston 334 through hollow portion 348. The first vertical intake passage 364 is linked to a first horizontal intake passage 365 and a second horizontal intake passage 366. See FIG. 5D. The first and second horizontal intake passages 365, 366 may have a first and second one-way intake valve 367, 368, respectively.

The first and second one-way intake valves 367, 368 are one-way valves that enable fluid to flow only from the evacuation volume 307 into the first and second evacuation chambers 336, 338, respectively. The first evacuation chamber 336 pulls fluid from the evacuation volume 307 via the first horizontal intake passage 365 as the piston 334 travels downward in the direction B relative to the sealed volume 332. The second evacuation chamber 338 pulls fluid from the evacuation volume 307 via the second horizontal intake passage 366 as the piston 334 travels upward in the direction A relative to the sealed volume 332. The piston 334 has air openings 369, 370, with one air opening 369 opening to the first evacuation chamber 336 and one air opening 370 opening to the second evacuation chamber 338. Air may pass through the air openings 369, 370 to enter the first and second evacuation chambers 336, 338 through the first and second one-way intake valves 367, 368, as shown by the dashed-line flow paths in FIG. 5D.

Air in the first and second evacuation chambers 336, 338 may exit by passing through the air openings in the piston 334. As the piston 334 reciprocates in the sealed volume 332, air in the first evacuation chamber 336 may pass through air opening 369 in the top of the piston 334 (see FIG. 5C), through a first one-way exhaust valve 372, through a first horizontal exhaust passage 373, and to a vertical exhaust passage 374 (see FIGS. 3C and 5E). Likewise, reciprocation of the piston 334 in the sealed volume 332 in the opposite direction may cause air in the second evacuation chamber 338 to pass through air opening 370 in the bottom of the piston 334 (see FIG. 5C), through a second one-way exhaust valve 376, through a second horizontal exhaust passage 377, and to the vertical exhaust passage 374 (see FIGS. 3C and 5E).

Air in the vertical exhaust passage 374 may escape into atmosphere by passing through bottom portion 350 of the piston 334 between its inner surface and the compressible cylinder 356, then out of a vent opening 378 in the bottom cap 326 and through the bottom opening 362 of the vacuum pump 300. See FIG. 3C. Accordingly, air may be pumped from the evacuation volume 307 through the vacuum pump 300 as the piston 334 moves within the sealed volume 332. Air from the evacuation volume 307 is vented to atmosphere during each pump cycle, which may correspond to each step on the prosthesis to which the vacuum pump 300 is attached. Accordingly, walking on the prosthesis may continuously evacuate air from the evacuation volume 307, thereby preserving a low pressure condition within the evacuation volume 307 and maintaining connection between the socket 301 and the liner 305.

The compressible cylinder 356 or spring element may be used to bias the piston 334 and to absorb shock as the vacuum pump 300 is used. For example, the compressible cylinder 356 may be configured to apply a force to the bottom of the piston 334 in direction A as the compressible cylinder 356 is compressed. The compressible cylinder 356 may simultaneously apply a downward force against the bottom cup 360 that biases the piston 334 to be at the top of the sealed volume 332 within the shaft 304 when the pump 300 is not loaded. Thus, the section view of FIG. 3C shows the piston 334 at a mid-stroke position relative to its rest position within the sealed volume 332. At rest, the first evacuation chamber 336 has its minimum (e.g., nearly zero) volume due to the piston 334 being positioned vertically high up and in contact with the bottom surface of top cap 324, and the second evacuation chamber 338 has its maximum volume. At full stroke, the first evacuation chamber 336 has its maximum volume, and the second evacuation chamber 338 has its minimum volume due to the piston 334 being near the bottom of the sealed volume 332 and near the top surface of the bottom cap 326. In some embodiments, the piston 334 does not come into contact the bottom cap 326 since doing so would cause impact forces to be transferred to the user's limb. Adjustment the preload of the compressible cylinder 356 using the bottom cup 360 and/or selecting a compressible cylinder 356 with an appropriate spring rate may prevent contact from occurring.

FIG. 3D is a top section view taken through section lines 3D-3D in FIG. 3A. FIGS. 3B-3D and 4 illustrate a resilient rotation restriction assembly that may be used in the vacuum pump 300. The rotation restriction assembly may comprise a plurality of rigid blocks 380 positioned on the inner wall 318 of the housing 302, a plurality of rigid blocks 382 positioned on the outer wall 320 of the shaft 304, and a plurality of resilient blocks 384 positioned between the internal surface of the housing 302 and the external surface of the shaft 304. See FIGS. 3B and 3D. The rigid blocks 380, 382 may be securely affixed to their respective walls 318, 320. The rigid blocks 380, 382 may be circumferentially spaced around the walls 318, 320 and may, upon assembly of the pump 300 have substantially equal longitudinal positions within the pump 300. As shown in FIG. 3D, the rigid blocks 380 on the inner wall 318 may be positioned about 180 degrees apart from each other relative to a longitudinal axis of the housing 302, and the rigid blocks 382 on the outer wall 320 may be positioned about 180 degrees apart from each other relative to a longitudinal axis of the shaft 304.

Each of the plurality of resilient blocks 384 may be positioned between the walls 318, 320 without being attached thereto. Upon assembly of the vacuum pump 300, the resilient blocks 384 may be positioned circumferentially between the rigid blocks 380, 382. See FIGS. 3B and 3D. Accordingly, at least one resilient block 384 may be positioned between each adjacent pair of rigid blocks 380, 382. Each of the resilient blocks 384 may comprise at least one chamfer 386. The chamfer 386 may help guide the rigid blocks 380, 382 to be positioned between the resilient blocks 384 as the vacuum pump 300 is assembled.

During use of the vacuum pump 300, the prosthetic shaft 112 may apply a torque to the shaft 304 (or housing 302) that urges the shaft 304 to rotate around its longitudinal axis relative to the housing 302. A small amount of relative rotation between the shaft 304 and the housing 302 may be desirable for user comfort, but large angular displacement between the shaft 304 and housing 302 may cause misalignment of the prosthetic. Accordingly, the resilient rotation assembly may be used with the vacuum pump 300 to address these concerns.

When a torque is applied to the shaft 304, the shaft 304 may be urged to rotate within the housing 302. This may also cause the rigid blocks 382 on the outer wall 320 to rotate around the longitudinal axis of the shaft 304. Rotation of the rigid blocks 382 urges them circumferentially toward rigid blocks 380 on the inner wall 318 of the housing 302. The rigid blocks 380, 382 accordingly apply compressive forces to the resilient blocks 384 that are positioned in the path of rotation of the rigid blocks 382. The rigid blocks 380, 382 may comprise a rigid material (e.g., a metal), and the resilient blocks 384 may comprise a comparatively more resilient material (e.g., a rubber or resilient polymer). Accordingly, the compressive forces on the resilient blocks 384 may cause the resilient blocks 384 to deform and compress between the rigid blocks 380, 382. The compressibility of the resilient blocks 384 may allow a degree of relative rotation between the housing 302 and shaft 304 but may also limit the amount of relative rotation between those parts. In some embodiments, about 7 degrees of rotation may be allowed by elastic compression of the resilient blocks 384 during normal walking gait. When subjected to more extreme torsional loads, for example when a user is golfing, about 10 degrees to about 40 degrees of rotation may be allowed by the elastic compression. When the torque on the shaft 304 (or housing 302) is released, the resilient blocks 384 may resiliently apply forces to the rigid blocks 380, 382 that cause the rigid blocks 380, 382 to circumferentially move back to their rest positions. Thus, the resilient blocks 384 automatically realign the limb after rotational deflection between the shaft 304 and housing 302.

FIG. 4 is an exploded view of the vacuum pump 300. The vacuum pump 300 includes subassemblies of the housing 302 and the shaft 304. The vacuum pump 300 may additionally and/or alternatively include assemblies and/or components not disclosed herein.

FIG. 4 shows a plurality of housing teeth 400 positioned circumferentially around the top of the housing 302. The housing teeth 400 may engage teeth 402 positioned around the bottom surface of the cap 306. See FIG. 3C. Thus, when the vacuum pump 300 is attached to the socket 301 (and cap 306), the teeth 400, 402 may engage each other to prevent rotation between the housing 302 and the socket 301. By preventing rotation between the housing 302 and the socket 301, the threaded member 308 may be threaded and tightened into place against the threads of the cap 306 more easily and without slippage of the housing 302 relative to the socket 301. Furthermore, the teeth 400, 402 ensure that the housing 302 and socket 301 remain in place relative to each other, even when torque is applied to the socket 301 or housing 302 that would urge one of them to rotate relative to each other around their common longitudinal axis. Torque applied to the housing 302 therefore would not loosen the connection between the housing 302 and the socket 301 since they are held together by the threaded member 308.

The plurality of teeth 400, 402 also allow the user to select a plurality of different predetermined relative angular positions for the housing 302 relative to the socket 301 when the two are joined by the threaded member 308. This capability would not be possible if the housing 302 was directly threaded to the cap 306 since threads on the housing 302 would need to be rotated to be tightened against the cap 306, and the final rotated position of the housing 302 relative to the cap 306 would not be easily predetermined or set by the user due to the threads.

Figure 5A:
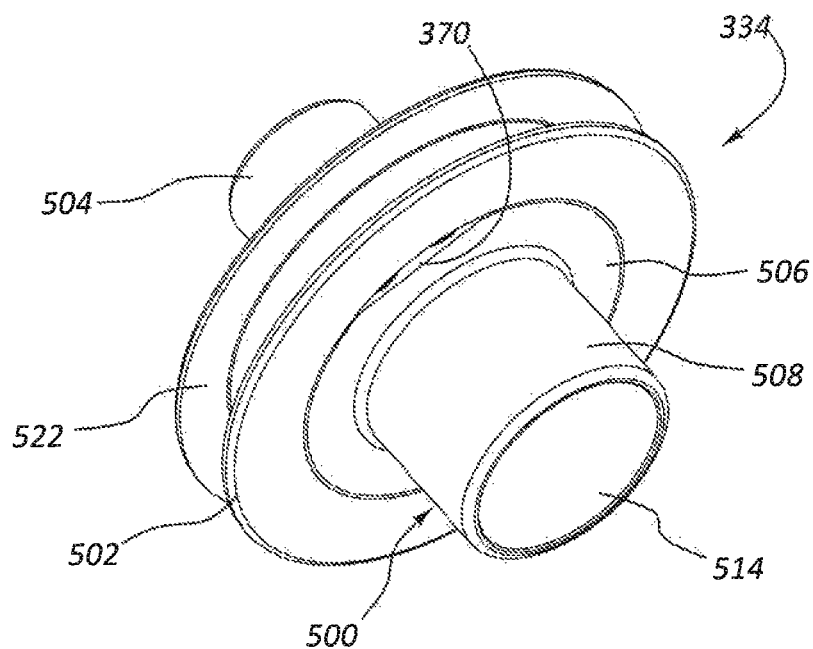
FIG. 5A is an perspective view of an example piston for use in the vacuum pumps disclosed herein.
Figure 5B:
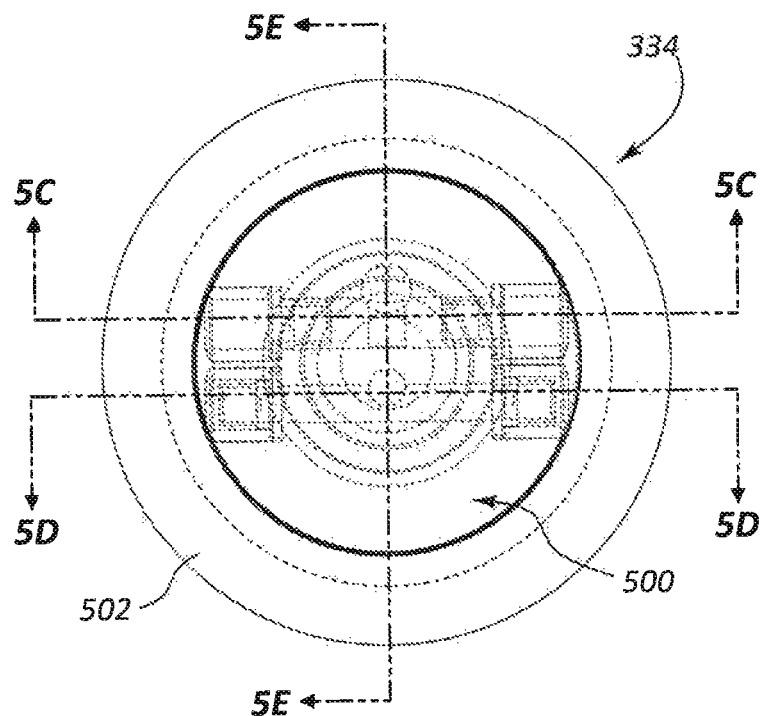
FIG. 5B is a top view of the piston shown in FIG. 5A.
Figure 5C:
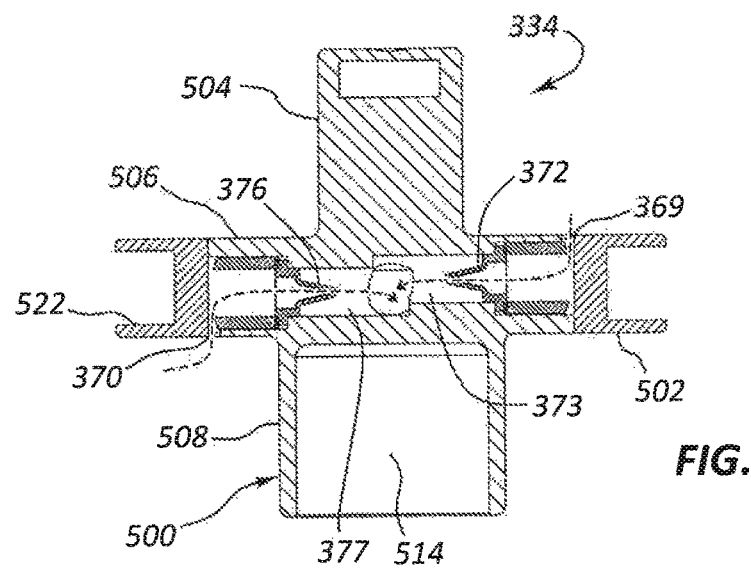
FIG. 5C is a cross-sectional view of the piston shown in FIG. 5A taken along cross-section indicators 5C-5C in FIG. 5B.
Figure 5D:
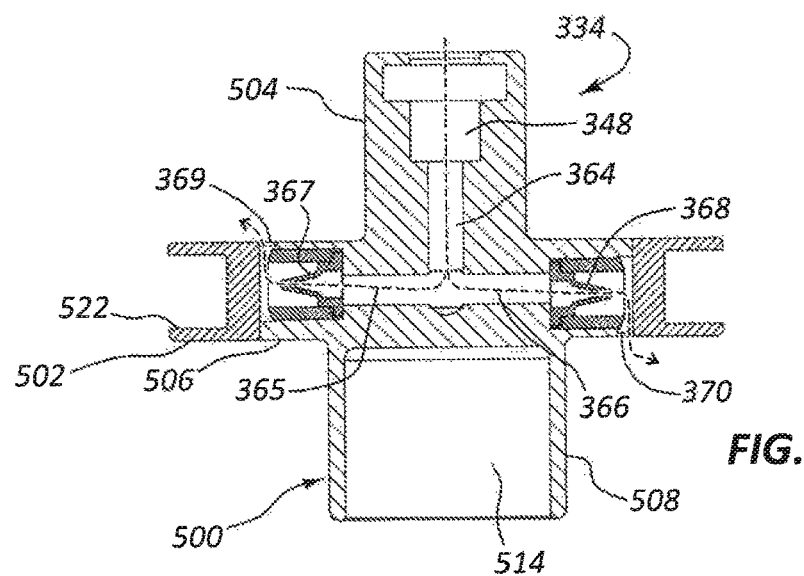
FIG. 5D is a cross-sectional view of the piston shown in FIG. 5A taken along cross-section indicators 5D-5D in FIG. 5B.
Figure 5E:
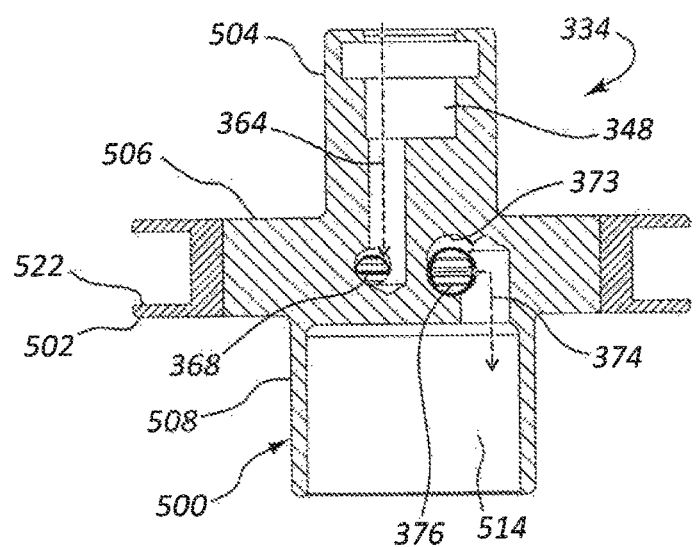
FIG. 5E is a cross-sectional side view of the piston shown in FIG. 5A taken along cross-section indicators 5E-5E in FIG. 5B.

FIG. 5A is a perspective view of the piston 334 of the vacuum pump 300. The piston 334 may comprise a two-piece assembly that incorporates one or more fluid passages. FIG. 5B is a top down view of the piston 334. FIG. 5C is a cross-sectional view of the piston 334 along section lines 5C-5C in FIG. 5B. FIG. 5D is a cross-sectional view of the piston 334 along section lines 5D-5D in FIG. 5B. FIG. 5E side section view of the piston 334 taken through section lines 5E-5E in FIG. 5B.

As shown in FIGS. 5C and 5D, the piston 334 may comprise a two-piece assembly including an inner piece 500 and an outer piece 502. The inner piece 500 may contain various passages for transferring fluid, as described above. The inner piece 500 may comprise multiple cylindrical sections. For example, the inner piece 500 may include an upper section 504, a middle section 506, and a lower section 508. The upper section 504 has the smallest cylindrical diameter and connects to the cap 306. The middle section 506 has a larger diameter than the upper section 504 and interfaces with the outer piece 502. The lower section 508 has a smaller diameter than the middle section 506 but a larger diameter than the upper section 504. The lower section 508 contacts the compressible cylinder 356. The size of diameters and correlation between the sizes of diameters may vary. For examples, the diameters may be greater than, smaller than, or equal to other diameters. In some instances, there may be greater or fewer sections of the inner piece 500.

In this embodiment, the upper section 504 may comprise the hollow portion 348. The lower section 508 may include a lower cylindrical void 514, within which the piston 334 may receive the compressible cylinder 356. See FIG. 3C. The compressible cylinder 356 may apply a force to the lower cylindrical void 514 to bias the piston 334 into contact with the cap 306.

The outer piece 502 may be a flattened torus. The outer piece 502 may be press-fit onto the inner piece 500. The flattened torus may alternatively be adhered or otherwise fastened to the inner piece 500. In some embodiments, an outer diameter 520 of the outer piece 502 may incorporate a substantially rectangular groove 522. The groove 522 may incorporate a compressible seal. The compressible seal may fluidly separate a first chamber and a second chamber of a seal volume in a vacuum pump.

Figure 6:
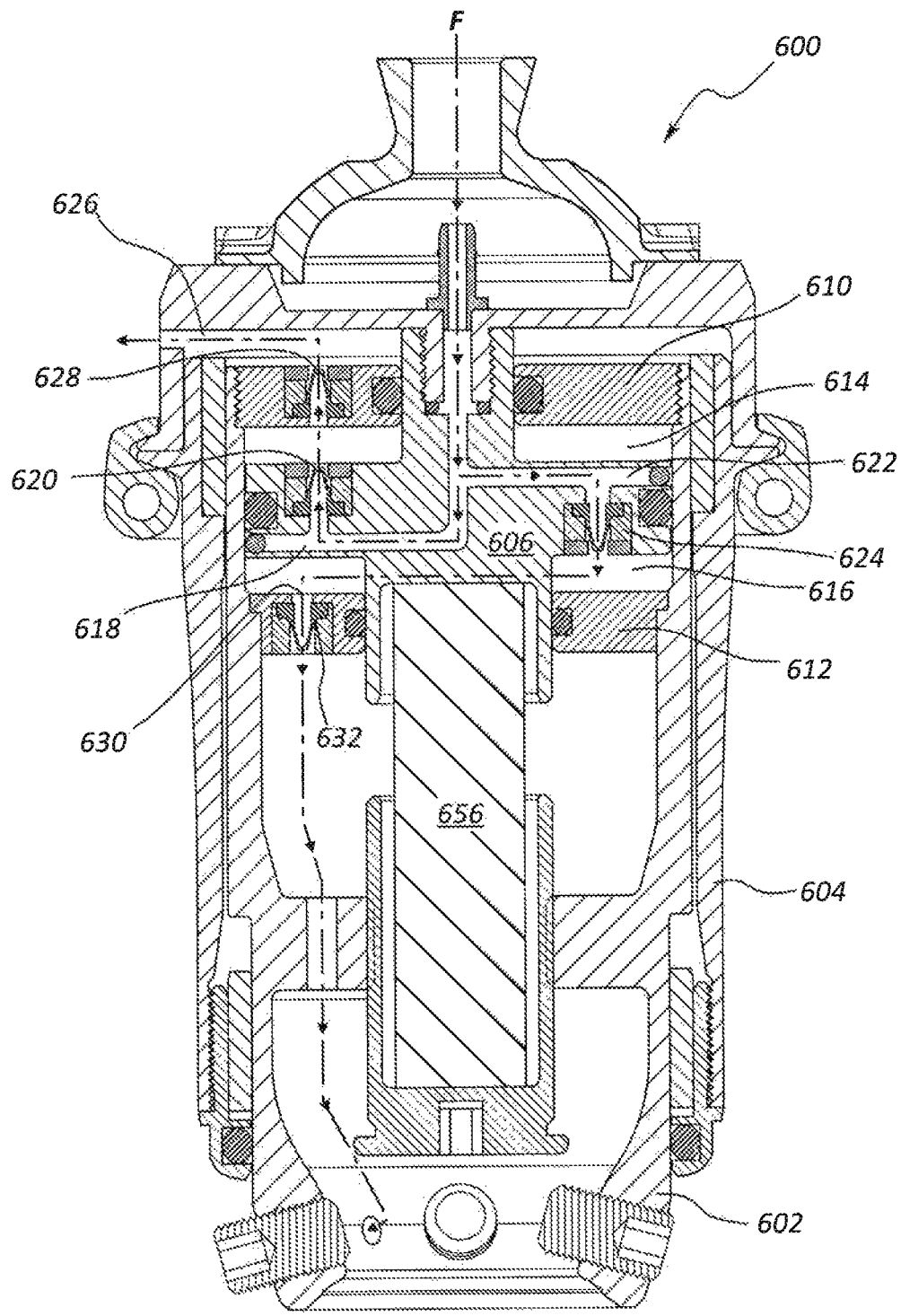
FIG. 6 is a cross-sectional view of an example parallel vacuum pump in a first operational state in accordance with the present disclosure.

FIG. 6 is an alternative embodiment of a parallel vacuum pump 600. The alternative embodiment may incorporate a shaft 602 and a housing 604. The parallel vacuum pump 600 may incorporate similar features of the vacuum pump 300 described with reference to FIGS. 3A-3C. For example, a piston 606 may be located within a sealed volume formed within the shaft 602.

The sealed volume may be formed by the housing 604, a top cap 610, and a bottom cap 612. The piston 606 may separate the sealed volume into a first chamber 614 and a second chamber 616. In this embodiment, the piston 606 may be a one-piece piston that incorporates one or more intake valves. For example, the piston 606 may include a first intake passage 618 that fluidly connects the first chamber 614 to an evacuation volume (e.g., evacuation volume 204, 224). The first intake passage 618 may include a first intake valve 620 that may be a one-way fluid valve enabling fluid flow in a single direction. The piston 606 may additionally include a second intake passage 622, which may fluidly connect the second chamber 616 to the evacuation volume. The second intake passage 622 may include a second intake valve 624. The second intake valve 624 may be a one-way valve enabling fluid flow in a single direction.

The piston 606 is shown in a mid-stroke position. As shown, the piston 606 is centrally located within the sealed volume. This situation may arise as the piston 606 cycles during use. A spring member 656 may otherwise bias the piston 606 and top cap 610 together. As shown, the first chamber 614 and the second chamber 616 have substantially similar volumes. However, as the piston 606 reciprocates within the sealed volume, the respective volumes of the first and second chambers 616, 618 will vary.

A first exhaust passage 626 fluidly couples the first chamber 614 to atmosphere. The first exhaust passage 626 may enable fluid to exit the first chamber 614. A first exhaust valve 628 may be located within the first exhaust passage 626. The first exhaust valve 628 may be a one-way valve enabling fluid flow in a single direction, namely a direction away from the first chamber 614.

A second exhaust passage 630 fluidly couples the second chamber 616 to atmosphere. The second exhaust passage 630 may enable fluid to exit the second chamber 616. A second exhaust valve 632 may be located within the second exhaust passage 630. The second exhaust valve 632 may be a one-way valve enabling fluid flow in a single direction, namely a direction away from the second chamber 616.

Figure 7:
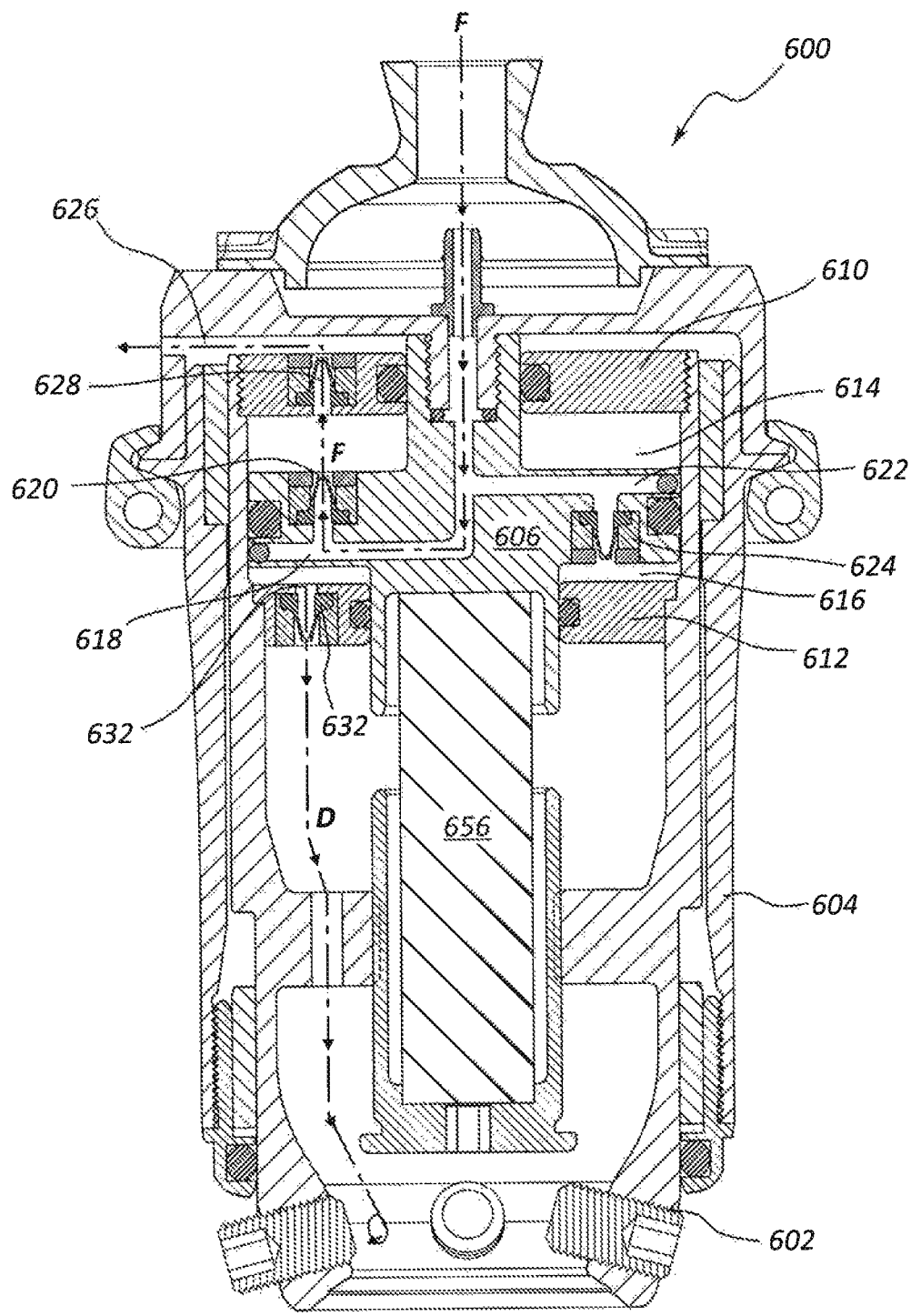
FIG. 7 is a cross-sectional view of the parallel vacuum pump shown in FIG. 6 in a second operational state.

FIG. 7 shows the parallel vacuum pump 600 during a down stroke of the vacuum cycle. The down stroke may occur when a user puts weight on the prosthetic device during use. In alternative embodiments, the down stroke may occur when the piston is cycled using a power source. As shown, the down stroke causes a volume of the second chamber 616 to decrease as a volume of the first chamber 614 increases. The fluid in the second chamber 616 exits the second chamber 616 via the second exhaust passage 630 in a direction D. The down stroke additionally causes the volume of the first chamber 614 to increase. The first chamber 614 pulls a fluid (e.g., air) from an evacuation volume, via the first intake passage 618 in a direction F.

Figure 8:
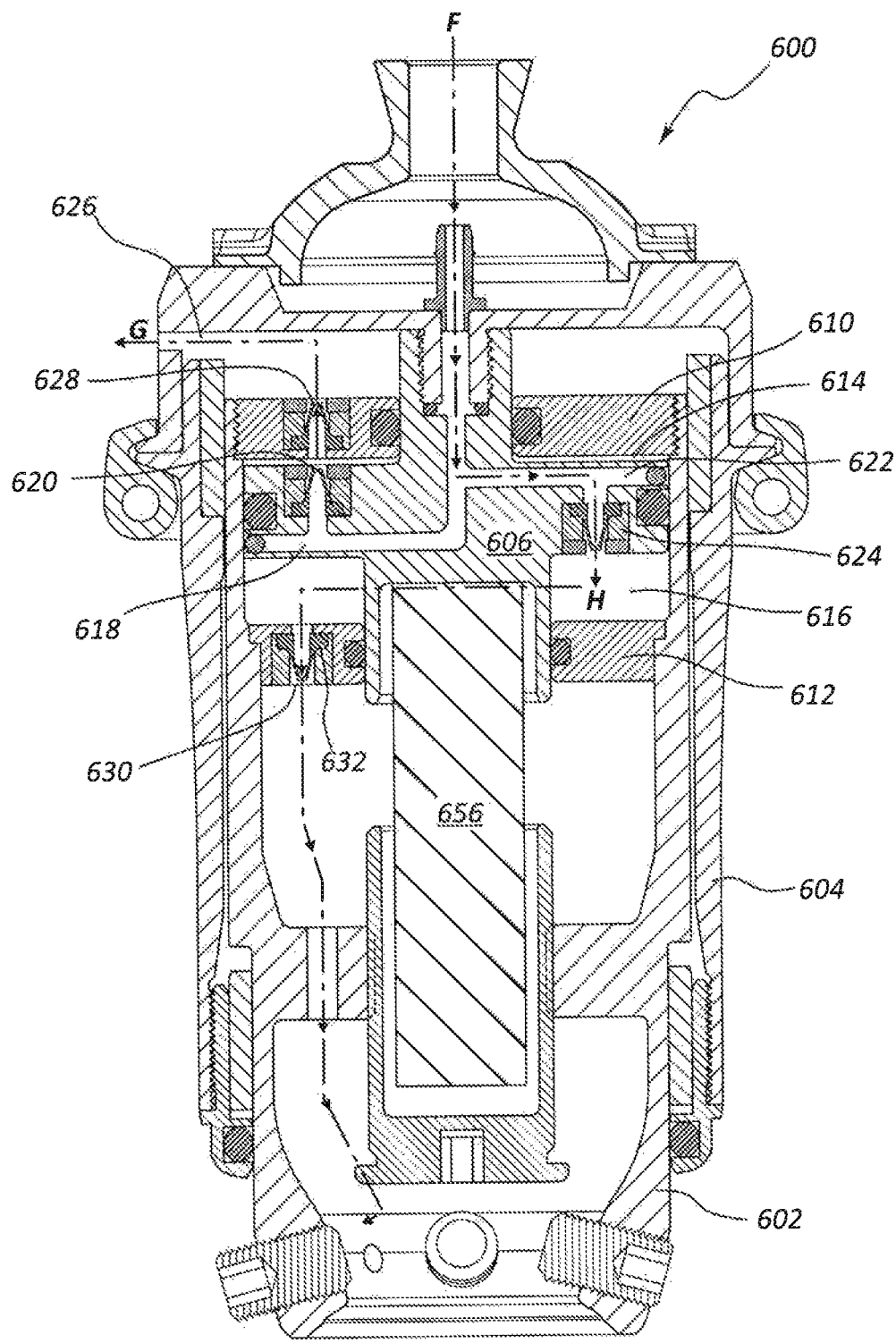
FIG. 8 is a cross-sectional view of the parallel vacuum pump shown in FIG. 6 in a third operational state.

FIG. 8 shows the parallel vacuum pump 600 during an up stroke of the vacuum cycle. The up stroke may occur when a user unloads weight on the prosthetic. This may occur when a user is walking or running. The spring member 656 causes a force that pulls on the vacuum pump and biases the piston 606 upwards toward the top cap 610. In alternative embodiments, the up stroke may occur when the piston is cycled using an electric motor. As shown, the up stroke causes a volume of the first chamber 614 to decrease as a volume of the second chamber 616 increases. The fluid in the first chamber 614 exits the first chamber 614 via the first exhaust passage 626 in a direction G. The up stroke additionally causes the volume of the second chamber 616 to increase. The second chamber 616 pulls a fluid (e.g., air) from an evacuation volume, via the second intake passage 622, in a direction H.

Figure 9:
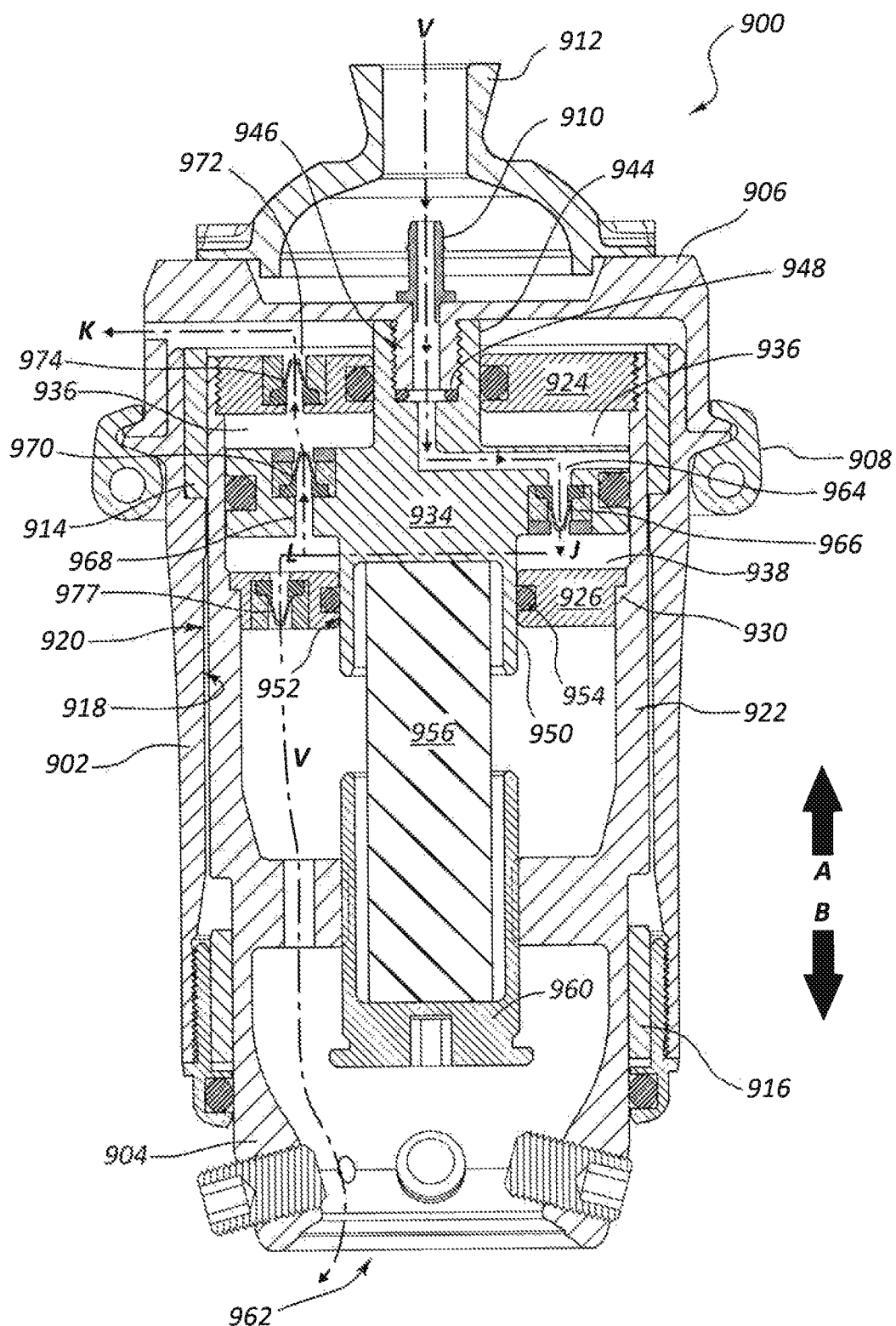
FIG. 9 is a cross-sectional view of an example series vacuum pump in accordance with the present disclosure.

FIG. 9 illustrates an example series vacuum pump 900. The series vacuum pump 900 comprises a housing 902 and a shaft 904. The shaft 904 moves in relation to the housing 902. The housing 902 may include a cap 906 that may be coupled to the housing 902 via one of more clamps 908. The housing 902 and cap 906 may alternatively be screwed together via mating threads, fastened together, adhered together, or otherwise coupled. The cap 906 may additionally comprise a barb 910 and a connector 912 that couples the series vacuum pump 900 to a socket (e.g., socket 108 shown in FIG. 1). The connector 912 may provide a mechanical connection between the series vacuum pump 900 and the socket. The barb 910 may provide a fluid connection between the series vacuum pump 900 and an evacuation volume (e.g., evacuation volume 204). The evacuation volume may be formed between a socket and a liner that is mounted to a residual limb positioned in the socket.

A first bearing 914 and a second bearing 916 provide an interface between the housing 902 and the shaft 904. The first bearing 914 and second bearing 916 may provide support between the shaft 904 and housing 902 as the shaft 904 and the housing 902 move in relation to each other. The bearings 914, 916 may maintain a working distance between an inner wall 918 of the housing 902 and an outer wall 920 of the shaft 904.

The shaft 904 may comprise a multi-piece assembly. For example, the shaft 904 may be an assembly comprising a body 922, a top cap 924, and a bottom cap 926. The top cap 924 and bottom cap 926 may be coupled to an internal wall 928 of the body 922. The bottom cap 926 may be tight-fit, screwed, adhered, or otherwise coupled to the body 922. In some embodiments, the bottom cap 926 may rest on a lip 930 on the internal wall 928 of the body 922. The top cap 924 may be coupled to a top of the body 922 of the shaft 904.

The top cap 924, bottom cap 926, and body 922 may form a sealed volume 932 (e.g., sealed volume, 206).

A piston 934 is positioned in the sealed volume 932 and may form two evacuation chambers within the sealed volume 932. For example, the piston 934 may be movably situated in the sealed volume 932 and may fluidly separate the sealed volume 932 into a first evacuation chamber 936 and a second evacuation chamber 938. A compressible seal 940 may be located on an outer diameter 942 of the piston 934. The compressible seal 940 may fluidly separate the first evacuation chamber 936 and the second evacuation chamber 938 while enabling the piston 934 to reciprocate inside the shaft 904.

The piston 934 is coupled to the cap 906. For example, the piston 934 may be threadably engaged with the cap 906 at a top portion 944 of the piston 934. In some embodiments, the top portion 944 of the piston 934 may connect to a cylinder 946 of the cap 906. In other embodiments, the top portion 944 of the piston 934 may extend through an opening of the top cap 924. In some embodiments, the joint may incorporate a compressible seal 948. The compressible seal 948 may maintain the sealed volume 932 by preventing bleed through the joint between top portion 944 and cylinder 946.

A bottom portion 950 of the piston 934 may pass through an opening 952 in the bottom cap 926. The opening 952 may incorporate a compressible seal 954, which may maintain the sealed volume 932 while enabling the bottom portion 950 of the piston 934 to pass through the opening 952. The bottom portion 950 of the piston 934 may be coupled to or abutting a spring element 956. The spring element 956 may be fairly rigid but act as a spring or dampening feature to the prosthetic. The spring element 956 may have a spring rate within a range of about 10 N/mm and about 350 N/mm. A bottom 958 of the spring element 956 may be coupled to fixture bottom cup 960.

The bottom cup 960 may keep the spring element 956 within the shaft 904. The prosthetic shaft may extend into an opening 962 in the body 922 of the shaft 904 and be coupled to the bottom of the shaft 904. The prosthetic shaft may be screwed, threaded, tight-fit, clamped, adhered, or otherwise attached thereto. In some embodiments, the prosthetic shaft and the series vacuum pump 900 may be easily separable for multiple reasons. For example, a user may utilize different prosthesis depending on activity. Alternatively, ease of separation may enable ease of maintenance and care for the series vacuum pump 900.

The piston 934, housing 902, and cap 906 may move in unison as an assembly in relation to the shaft 904 and top and bottom caps 924, 926. As the piston 934 moves within the sealed volume 932, the respective volumes of the first evacuation chamber 936 and the second evacuation chamber 938 vary. As the piston 934 moves in a direction A relative to the sealed volume 932, the volume of the first evacuation chamber 936 reduces and the volume of the second evacuation chamber 938 increases. As the piston 934 reciprocates and moves in a direction B relative to the sealed volume 932, the volumes of the first evacuation chamber 936 and second evacuation chamber 938 may again change, with the volume of the first evacuation chamber 936 increasing and the volume of the second evacuation chamber 938 decreasing. In one embodiment, the piston 934 may be powered by an electrical motor (not shown). In another embodiment, if the prosthesis is a prosthetic leg, the piston 934 may move down in direction B relative to the sealed volume 932 when a person puts weight on the prosthesis. When the person takes a step and the weight is released, the piston 934 may move upward in direction A relative to the sealed volume 932.

In this instance, the series vacuum pump 900 is a series pump, meaning the second evacuation chamber 938 pulls a fluid from the evacuation volume and the first evacuation chamber 936 pulls fluid from the second evacuation chamber 938. The fluid may travel through one or more passages which may incorporate one or more one-way valves. The valves may enable fluid to only flow in a single direction.

For example, an intake passage 964 fluidly connects the second evacuation chamber 938 with the socket via barb 910. The intake passage 964 includes an intake valve 966. The intake valve 966 is a one-way valve that enables fluid to only flow from the evacuation volume into the second evacuation chamber 938. The second evacuation chamber 938 pulls fluid from the evacuation volume via the intake passage 964 in direction J as the piston 934 travels upward in the direction B.

As the piston 934 travels upward, a volume of the first evacuation chamber 936 is reduced. As the volume of the first evacuation chamber 936 is reduced, fluid from the first evacuation chamber 936 exits via an exhaust passage 972 in a direction K. The exhaust passage 972 may have an exhaust valve 974 that may enable single direction fluid flow. For example, the exhaust valve 974 may enable fluid to only flow in the direction K.

As the piston 934 reciprocates and travels downward in the direction B, the volumes of the first evacuation chamber 936 and the second evacuation chamber 938 change. As the volume of the second evacuation chamber 938 decreases, fluid travels from the second evacuation chamber 938 into the first evacuation chamber 936 via a connector passage 968 along a portion of the path labeled L. The connector passage 968 may include a connector valve 970 which may enable fluid flow in path L. Air from the second evacuation chamber 938 may also exhaust from the second evacuation chamber 938 via a one-way valve 977 along path V to atmosphere. The series vacuum pump 900 with the arrangement shown in FIG. 9 will act to generate a higher pressure differential between the evacuation volume and atmosphere than a parallel pump configuration.

Figure 10:
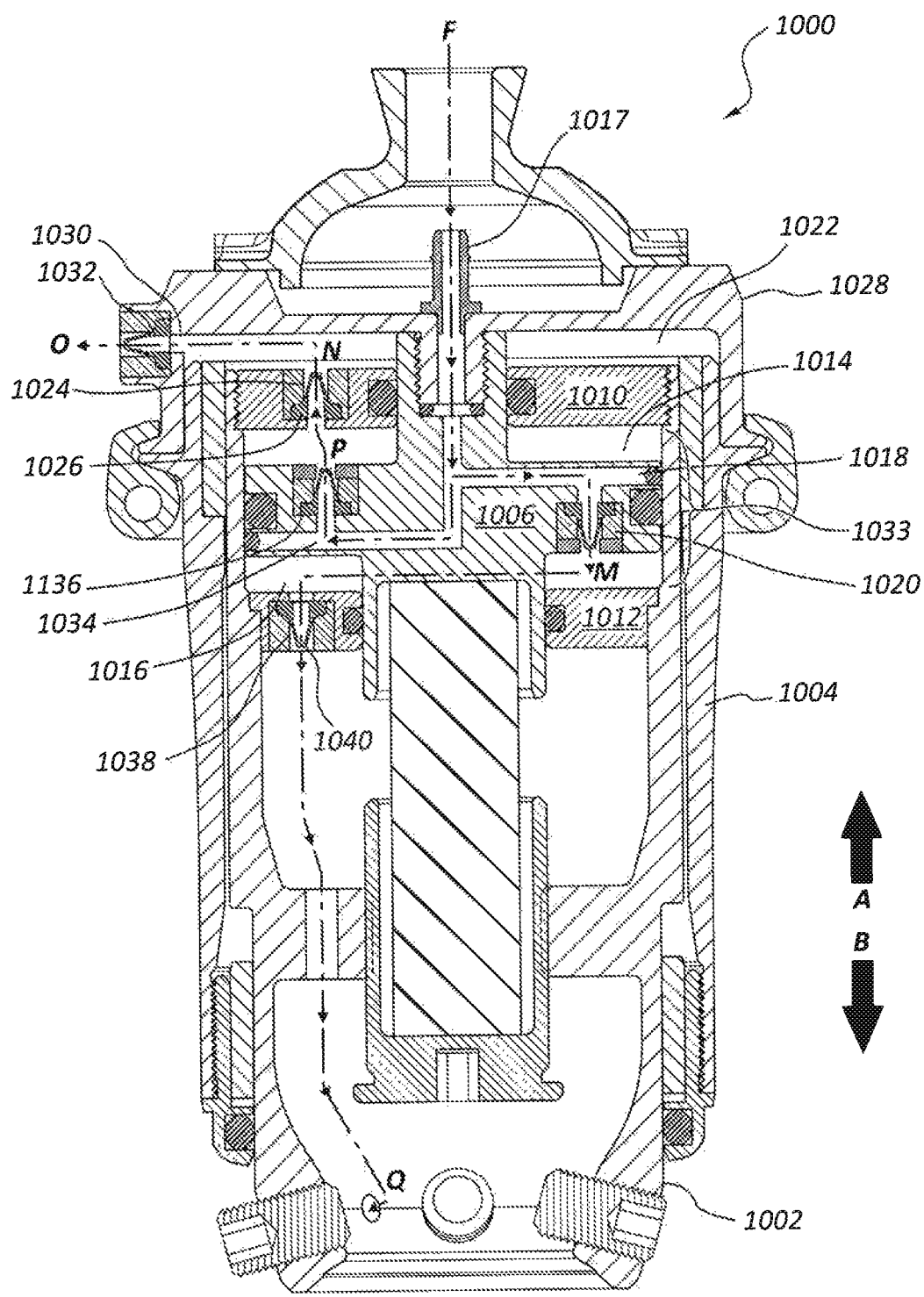
FIG. 10 is a cross-sectional view of an example combination parallel and series vacuum pump in accordance with the present disclosure.

FIG. 10 may be a cross-sectional view of an exemplary vacuum pump 1000 that is a combination parallel and series pump. The vacuum pump 1000 may incorporate similar features of the vacuum pump 300, 900 described with reference to FIGS. 3A-3C and 9. For example, a piston 1006 may be located within a sealed volume formed within the shaft 1002. A cap 1028 may be clamped, or otherwise removably affixed to a housing 1004.

The sealed volume may be formed by the shaft 1002, a top cap 1010, and a bottom cap 1012. The piston 1006 may separate the sealed volume into a first series chamber 1014 and a parallel chamber 1016. In this embodiment, the piston 1006 may be a one-piece piston that incorporates one or more intake valves. In other embodiments, the piston 1006 may comprise a two-piece design as described with reference to FIGS. 5A-5D. In either design, the piston 1006 may incorporate passages fluidly connecting various chambers. For example, the piston 1006 may include a parallel intake passage 1018 that fluidly connects the parallel chamber 1016 to an evacuation volume (e.g., evacuation volume 204/224 via barb 1017). The parallel intake passage 1018 may include a parallel intake valve 1020 that may be a one-way fluid valve enabling fluid flow in a single direction M. As the piston travels upward in the direction B relative to sealed volume 1033, the volume of the parallel chamber 1016 may increase as it pulls fluid from the evacuation volume along the path in the direction M.

As the volume of parallel chamber 1016 increases, the volume of the first series chamber 1014 decreases. As the piston 1006 travels upward in a direction A relative to sealed volume 1033, the fluid in the first series chamber 1014 exhausts into a second series chamber 1022 via a connection passage 1024 in a direction N. The connection passage 1024 includes a connection valve 1026 that enables one-way fluid flow indicated in the direction N. The second series chamber 1022 may be formed between the cap 1028 and the shaft 1002. The cap 1028 and the shaft 1002 may form a second sealed volume as the second series chamber 1022. As the piston 1006 travels upward in direction A relative to sealed volume 1033, the fluid in the first series chamber 1014 is pushed into the second series chamber 1022 via connection passage 1024. As this fluid is pushed into the second series chamber 1022, a pressure inside the second series chamber 1022 increases as this fluid merges with fluid existing within the second series chamber 1022. The increase in pressure in the second series chamber 1022 forces fluid to exhaust the second series chamber 1022 via a first exhaust passage 1030 in a direction O. The first exhaust passage 1030 may include an first exhaust valve 1032 is pushed into atmosphere. The first exhaust valve 1032 may enable fluid flow in a single direction O.

The piston 1006 then reciprocates within the sealed volume 1033 and travels downward in a direction B relative to sealed volume 1033. As the piston 1006 moves downward, the volume of the parallel chamber 1016 decreases and the volume of the first series chamber 1014 increases. The first series chamber 1014 pulls fluid from the evacuation volume via a series intake passage 1034. The fluid may travel through the series intake passage 1034 in a direction P. The series intake passage 1034 may include a series intake valve 1036. The series intake valve 1036 may enable one-way fluid flow in a direction P. At the same time, as the piston 1006 travels downward in a direction B, the fluid located within the parallel chamber 1016 may exit the parallel chamber 1016 via the parallel exhaust passage 1038. The fluid may travel through the parallel exhaust passage 1038 past a parallel exhaust valve 1040 within the parallel exhaust passage 1038 and into atmosphere in a direction Q.

The combination series and parallel vacuum pump 1000 may realize the benefits of both a series vacuum pump and a parallel vacuum pump. Thus, the combination vacuum pump 1000 may quickly achieve a strong vacuum condition. The first series chamber 1014 and the parallel chamber 1016 may act as a parallel vacuum pump and may exhaust fluid from the evacuation volume as both chambers 1014, 1016 pull air from the same evacuation volume. At the same time, the first series chamber 1014 and the second series chamber 1022 may act in concert to achieve a higher pressure differential in the evacuation volume.

Figure 11:
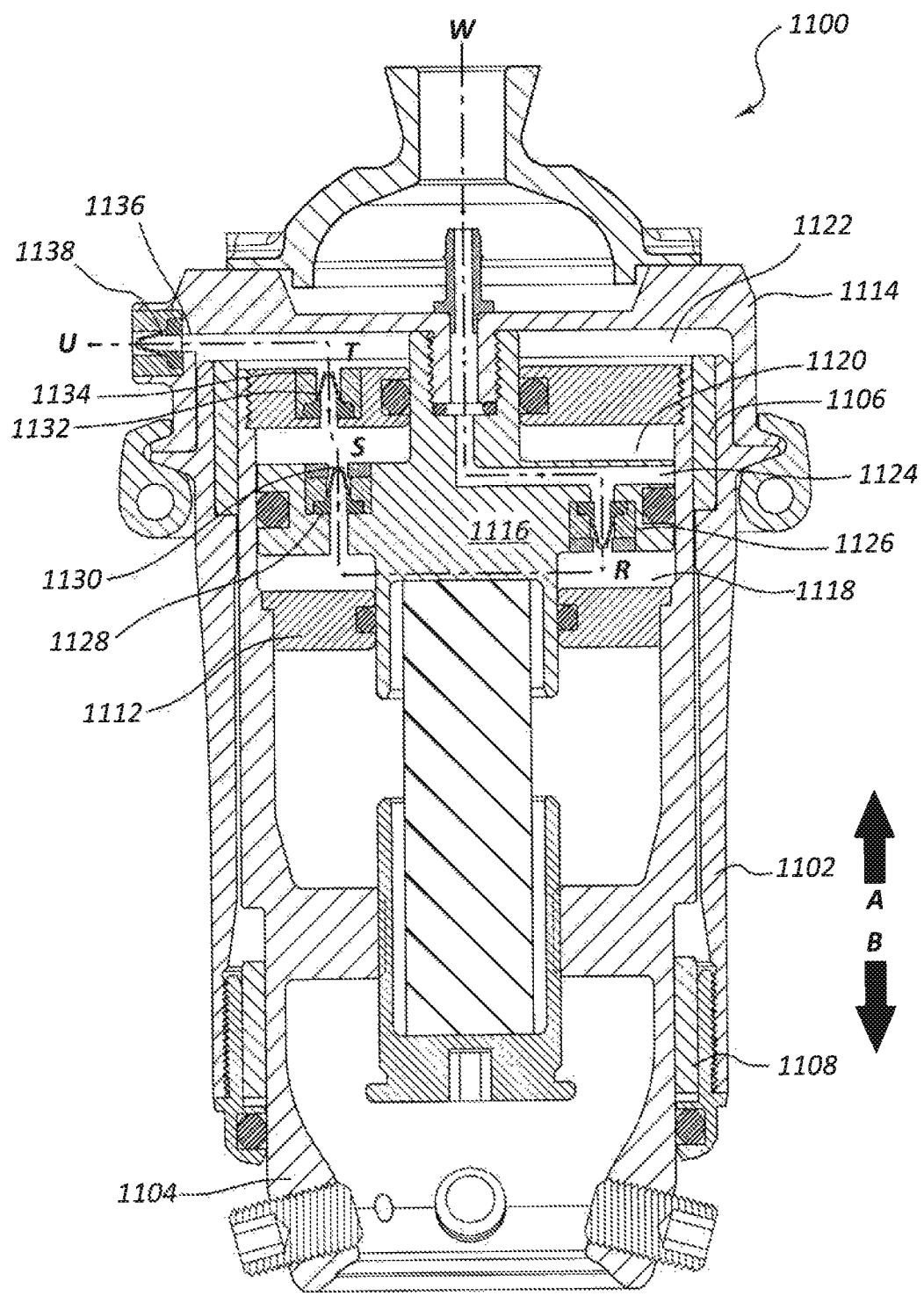
FIG. 11 is a cross-sectional view of an example three stage series vacuum pump in accordance with the present disclosure.

FIG. 11 is an example of a multiple state series vacuum pump 1100. The multiple stage series vacuum pump 1100 is similar to the combination series and parallel vacuum pump 1000 described with reference to FIG. 10. For example, the series vacuum pump 1100 includes a housing 1102 and a shaft 1104. The housing 1102 and the shaft 1104 may be separated by a first bearing 1106 and a second bearing 1108.

A top cap 1110 and bottom cap 1112 are coupled to the shaft 1104 and form a sealed volume. A piston 1116 may be situated in the sealed volume and may separate the sealed volume into two separate sealed volume chambers. A third sealed volume chamber may be formed between the top cap 1110 and a cap 1114 coupled to the housing 1102. The three volumes are a first chamber 1118, a second chamber 1120, and a third chamber 1122.

The first chamber 1118 is fluidly connected to an evacuation volume via an intake passage 1124. An intake valve 1126 is located in line with the intake passage 1124. The intake valve 1126 may be a one-way valve enabling fluid flow in a single direction. Fluid may travel from the evacuation volume into the first chamber 1118 via the intake passage 1124 in a direction R. Fluid in the first chamber 1118 may exit the first chamber 1118 and enter the second chamber 1120 via a first connection passage 1128 in a direction S. Fluid in the second chamber 1120 may exit the second chamber 1120 and enter the third chamber 1122 via a second connection passage 1132 in a direction T. Fluid in the third chamber 1122 may exit into atmosphere via an exhaust passage 1136 in direction U. Each of the passages may have a one-way valve that enables fluid to flow in a single direction. The first connection passage 1128 may have a first connection valve 1130 and the second connection passage may have the second connection valve 1134. The exhaust passage 1136 may have an exhaust valve 1138.

Movement of the piston 1116 may cycle the series vacuum pump 1100 and generate a vacuum condition in the evacuation volume. For example, as the piston 1116 moves upward in a direction A, fluid is pulled from the evacuation volume into the first chamber 1118 via the intake passage 1124 in a direction R. This movement causes fluid in the second chamber 1120 to exit the second chamber 1120 and enter the third chamber 1122 via first connection passage 1128 in direction S. This may cause pressure in the third chamber 1122 to increase. As the pressure increases, fluid may exit the third chamber 1122 into atmosphere via the exhaust passage 1136 in direction U. As the piston 1116 continues to cycle and move downward in a direction B, the volume of the first chamber 1118 decreases and the fluid in the first chamber 1118 is forced through the first connection passage 1128 into the increased volume of the second chamber 1120. The process then continues and the piston 116 travels upward again in the sealed volume.

The multiple stage series vacuum pump 1100 supercharges the vacuum and forces a little extra air into each chamber. This in turn increases the pressure differential in the evacuation volume. As a result, an even higher vacuum condition is achieved in the evacuation volume. The higher vacuum condition may result in better retention of the prosthetic to a residual limb.

Figure 12A:
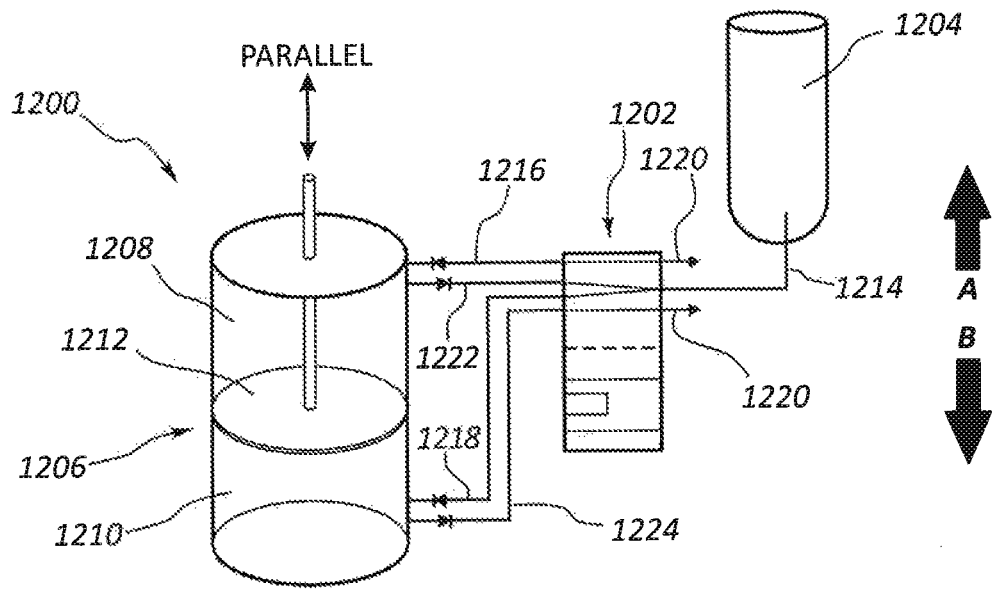
FIG. 12A is a schematic representation of a mode switching multi-chamber vacuum pump in parallel mode in accordance with the present disclosure.
Figure 12B:
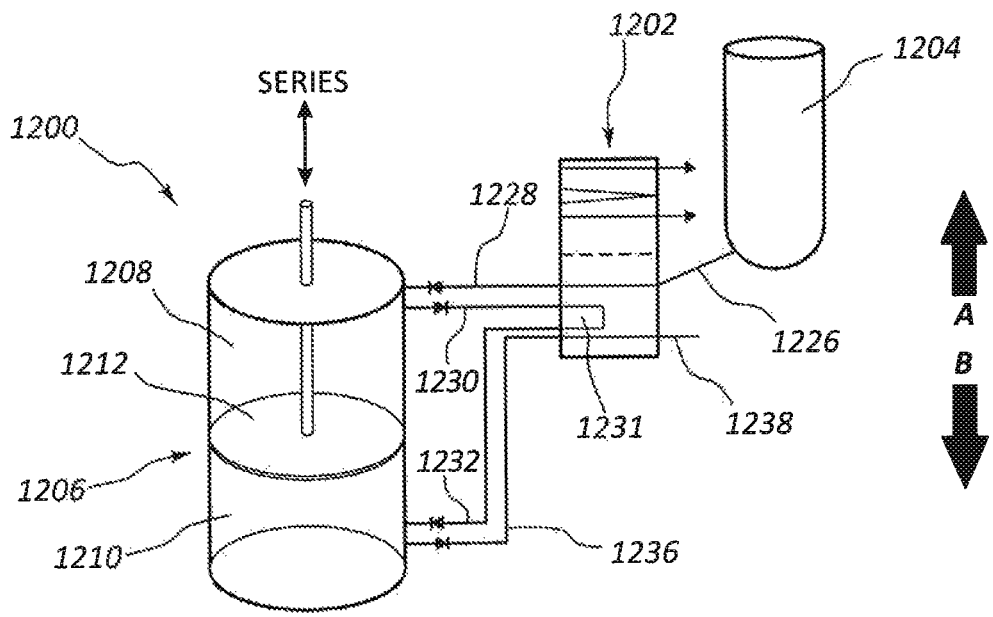
FIG. 12B schematic representation of a mode switching multi-chamber vacuum pump in series mode in accordance with the present disclosure.

FIGS. 12A and 12B illustrate example schematics of a vacuum pump 1200 that is switchable between a parallel configuration and a series configuration. In a switchable embodiment, the vacuum pump 1200 may be configured to operate in either a parallel configuration or a series configuration. A switch 1202 of the vacuum pump 1200 may be operable to facilitate the change between the series operation and the parallel operation.

FIGS. 12A and 12B include schematics of the vacuum pump 1200, the switch 1202 and an evacuation volume 1204. As mentioned previously, the evacuation volume 1204 may be situated between a residual limb and a socket (e.g., residual limb 104 and socket 108 shown in FIG. 1). In some embodiments, the residual limb may be fitted with a sock or a liner. A person may fit a residual limb with a sock or a liner prior to inserting the residual limb into a socket.

FIG. 12A is an example schematic of the switch 1202 in a parallel configuration. The vacuum pump 1200 may comprise a sealed volume 1206. The sealed volume 1206 may be separated into a first sealed volume chamber 1208 and a second sealed volume chamber 1210 by a piston 1212 that is located within the sealed volume 1206. As the piston 1212 reciprocates within the sealed volume 1206, a volume of the first chamber 1208 and a volume of the second chamber 1210 may vary.

The switch 1202 may be fluidly coupled to the evacuation volume 1204 via a parallel evacuation passage 1214. The parallel evacuation passage 1214 may enter the switch and split into two different passages: a first intake passage 1216 and a second intake passage 1218. The first intake passage 1216 may fluidly connect the first chamber 1208 to the evacuation volume 1204 when the switch 1202 in operating in parallel mode. Additionally, while the switch 1202 is in parallel mode, the second intake passage 1218 may fluidly couple the second chamber 1210 to the evacuation volume 1204.

The switch 1202 made additionally enable the first and second chambers 1208, 1210 to exhaust a fluid from the respective chambers via a parallel exhaust passage 1220. For example, a first exhaust passage 1222 may fluidly couple the first chamber 1208 to the parallel exhaust passage 1220. A second exhaust passage 1224 may fluidly couple the second chamber 1210 to the parallel exhaust passage 1220.

As the piston 1212 travels downward in a direction B, the volume of the first chamber 1208 increases and the volume of the second chamber 1210 decreases. As the volume of the first chamber 1208 increases, fluid is pulled from the evacuation volume 1204 via the parallel evacuation passage 1214 and first intake passage 1216. As the volume of the second chamber 1210 decreases, fluid is pushed from the second chamber 1210 into the second exhaust passage 1224 and parallel exhaust passage 1220 and then into atmosphere.

As the piston 1212 reciprocates and travels upward in a direction A, the volume of the second chamber 1210 increases and the volume of the first chamber 1208 decreases. As the volume of the second chamber 1210 increases, the second chamber 1210 pulls fluid from the evacuation volume 1204 via the parallel evacuation passage 1214 and second intake passage 1218. Likewise, as the volume of the first chamber 1208 decreases, the fluid in the first chamber 1208 is pushed into the first exhaust passage 1222 and into the parallel exhaust passage 1220.

FIG. 12B is an example schematic of the switch 1202 in a series configuration. In a series configuration, the switch 1202 may be fluidly coupled to the evacuation volume 1204 via an series evacuation passage 1226. The series evacuation passage 1226 may enter the switch 1202 and fluidly coupled to a chamber intake passage 1228. The chamber intake passage 1228 may fluidly connect the first chamber 1208 to the series evacuation passage 1226.

A first series connection passage 1230 may fluidly couple the first chamber 1208 to a series switch connection passage 1231 in the switch 1202. The switch connection passage 1231 may be fluidly connected to the second series connection passage 1232, which may be fluidly coupled to the second chamber 1210. The second chamber 1210 may exhaust a fluid via a series exhaust passage 1236. The series exhaust passage 1236 may be fluidly coupled to a series switch exhaust passage 1238. The series switch exhaust passage 1238 may be fluidly coupled to the second chamber 1210 to atmosphere.

Figure 13A:
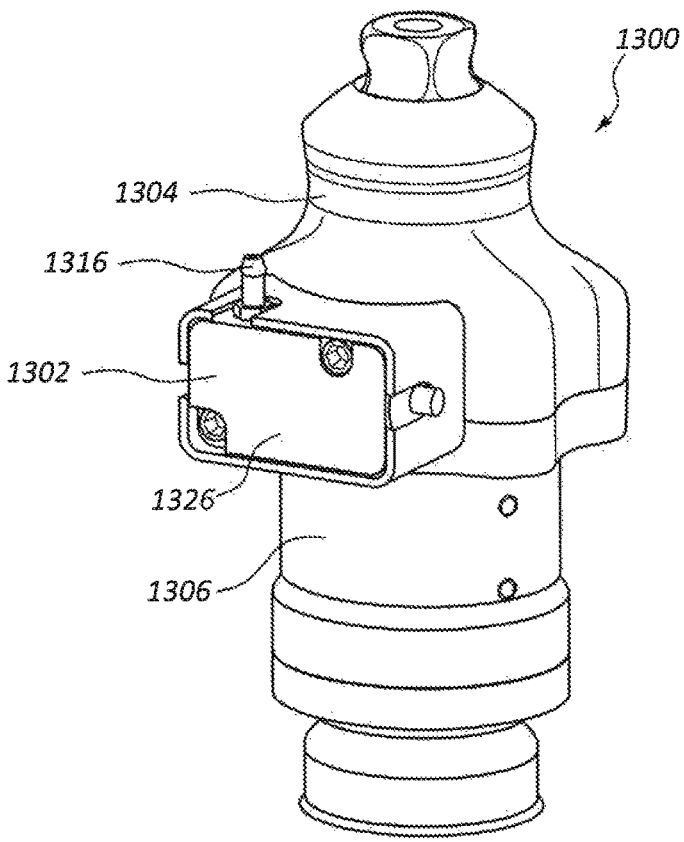
FIG. 13A is an perspective view of an example switching vacuum pump in accordance with the present disclosure.
Figure 13B:
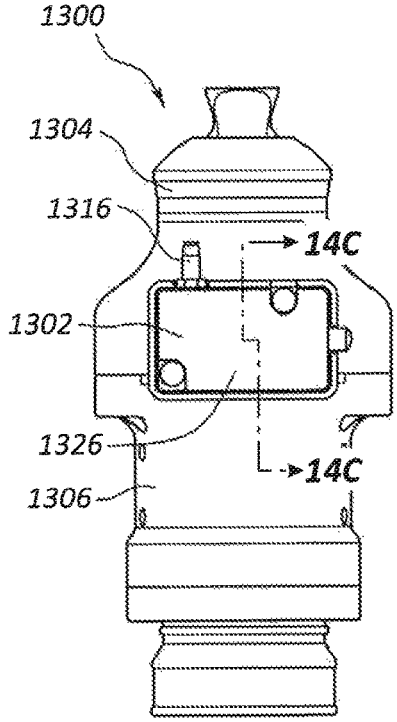
FIG. 13B is a side view of the switching vacuum pump shown in FIG. 13A.
Figure 13C:
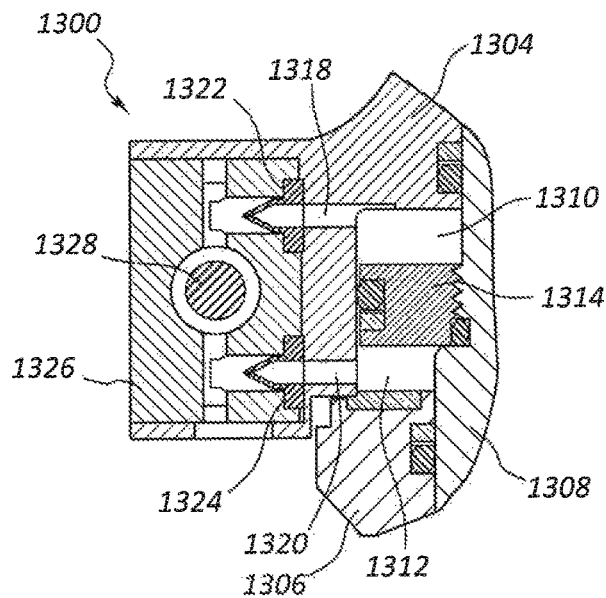
FIG. 13C is a partial cross-sectional view of the switching vacuum pump shown in FIG. 13B taken along cross-section indicators 13C-13C.

FIG. 13A is a perspective view of a switchable series/parallel vacuum pump 1300. FIG. 13C is a partial cutaway view of the switchable vacuum pump 1300 along line 13C-13C in FIG. 13B. FIG. 13B shows a side view of the switch 1302 situated between an upper housing 1304 and a lower housing 1306. A fluid connector 1316 may fluidly couple the switch 1302 to an evacuation volume.

The cross-sectional view in FIG. 13C shows the interplay of the switch 1302 with a first chamber 1310 and a second chamber 1312. FIG. 13C also includes a cross-sectional view of a shaft 1308 within upper housing 1304 and lower housing 1306 and a piston 1314. A first exhaust passage 1318 may fluidly couple the first chamber 1310 to the switch 1302. A second exhaust passage 1320 may fluidly couple the second chamber 1312 to the switch 1302. The first and second exhaust passages 1318, 1320 may respectively include a first exhaust valve 1322 and a second exhaust valve 1324. The exhaust valves 1322, 1324 may be one-way valves enabling fluid to only flow in a single direction out of the respective chambers 1310, 1312. More disclosure regarding the function of a housing 1304, 1306, shaft 1308, and piston 1314 compatible with the switch 1302 is provided in U.S. Pat. No. 7,744,653, the entire disclosure of which is hereby incorporated by reference.

Figure 14:
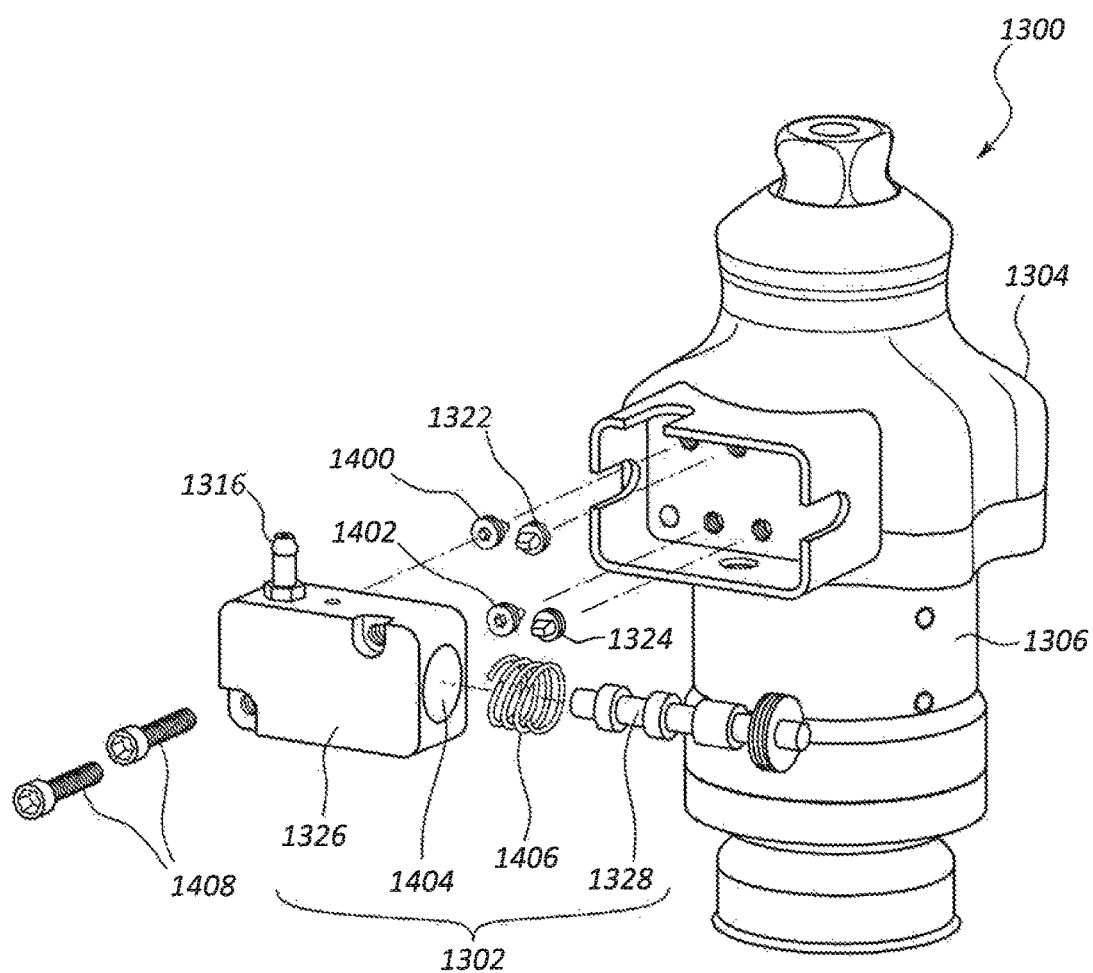
FIG. 14 is a partial exploded view of the vacuum pump shown in FIG. 13A.

The exhaust valves 1322, 1324 may be incorporated into either the upper housing 1304 (see FIGS. 13C and 14) or a switch housing 1326. A spool 1328 may be situated within the switch housing 1326. The spool 1328 may facilitate switching the switchable vacuum pump 1300 between series operation and parallel operation. An exploded version of the switch 1302 is shown in FIG. 14. FIG. 14 shows the switchable vacuum pump 1300 with an upper housing 1304 and a lower housing 1306.

The switch 1302 may include the switch housing 1326. The switch housing 1326 may include a fluid connector 1316. The fluid connector 1316 may fluidly couple the switchable vacuum pump 1300 to an evacuation volume. The switch housing 1326 may include the first and second exhaust valve 1322, 1324. In some embodiments the switch housing 1326 may additionally include a first intake valve 1400 and a second intake valve 1402. The spool 1328 may be insertable into an opening 1404 in the switch housing 1326. A spring 1406 may be inserted into the opening 1404 first and may work to move the spool 1328 between a series position and a parallel position. One or more set screws 1408 may or other fasteners may affix the switch 1302 to the switchable vacuum pump 1300.

Figure 15:
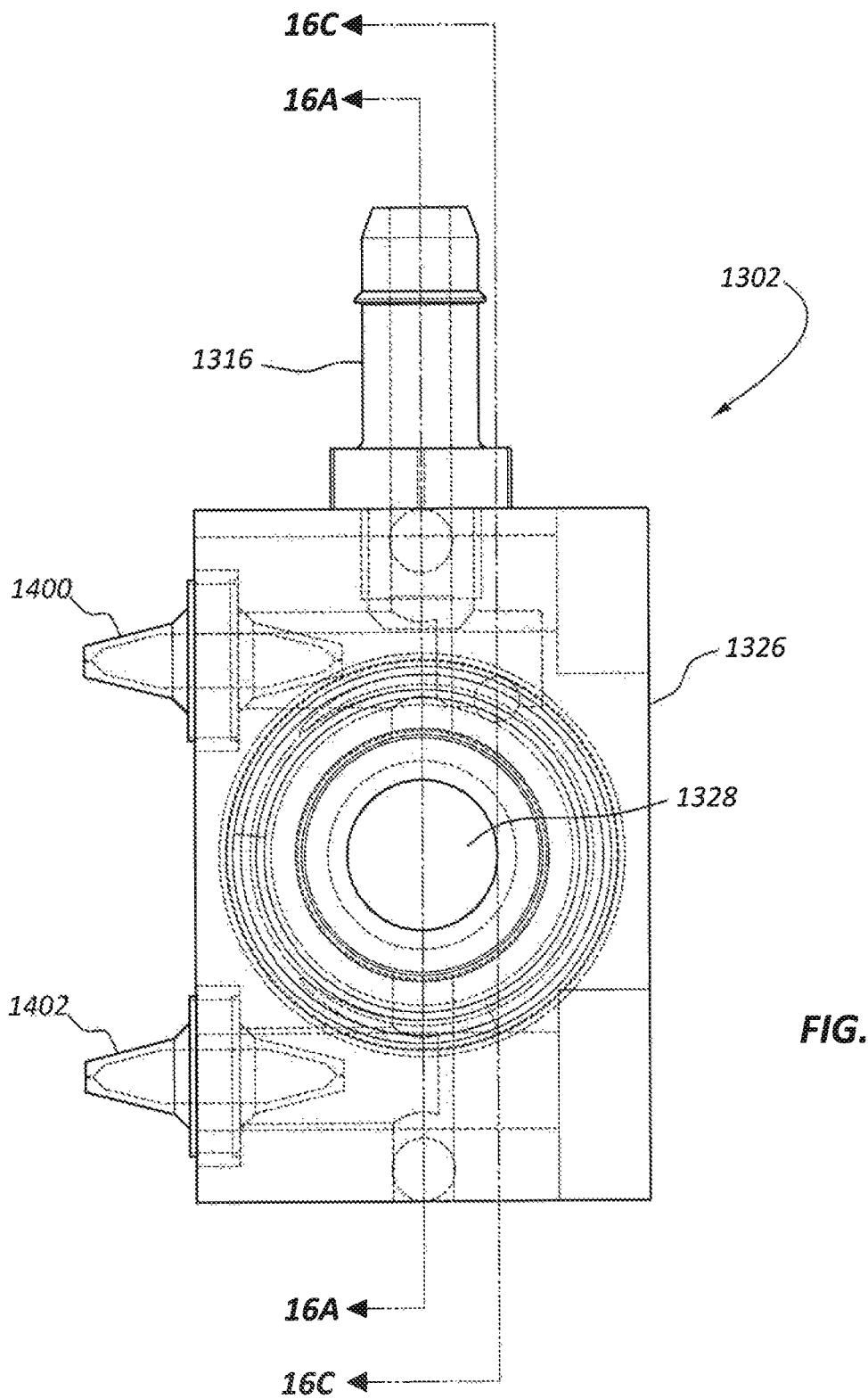
FIG. 15 is a side view of an example switch for use in a vacuum pump in accordance with the present disclosure.
Figure 16A:
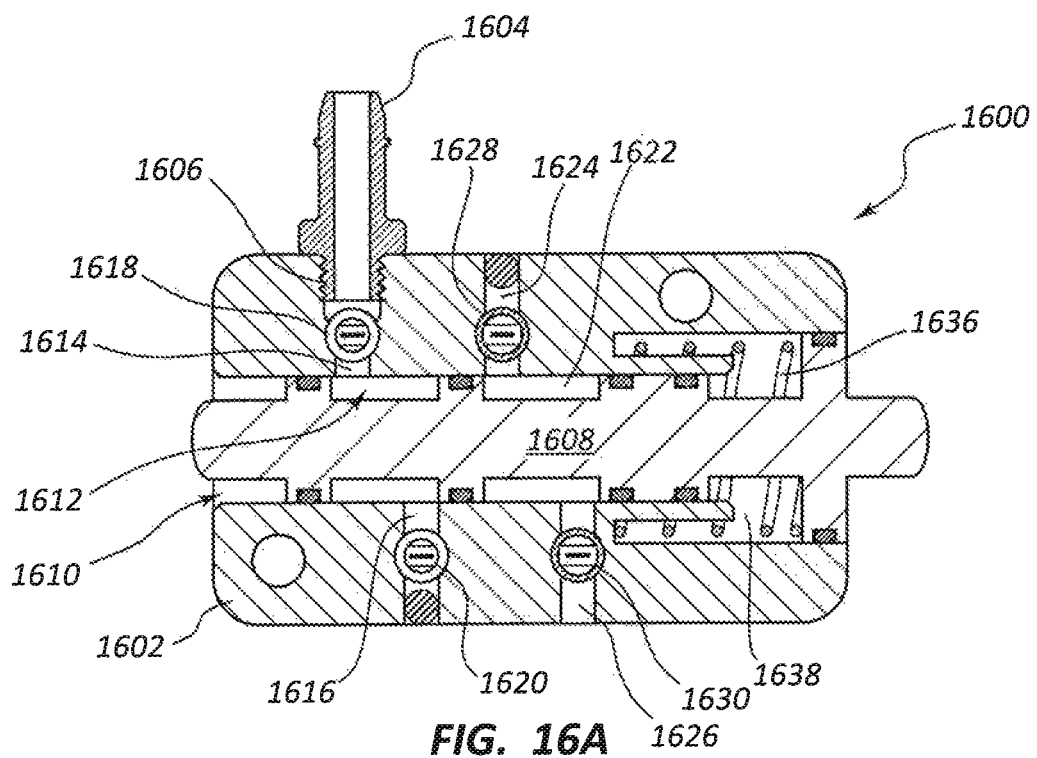
FIG. 16A is a cross-sectional view of the switch shown in FIG. 15 taken along cross-section indicators 16A-16A, the switch being arranged in a parallel mode.
Figure 16B:
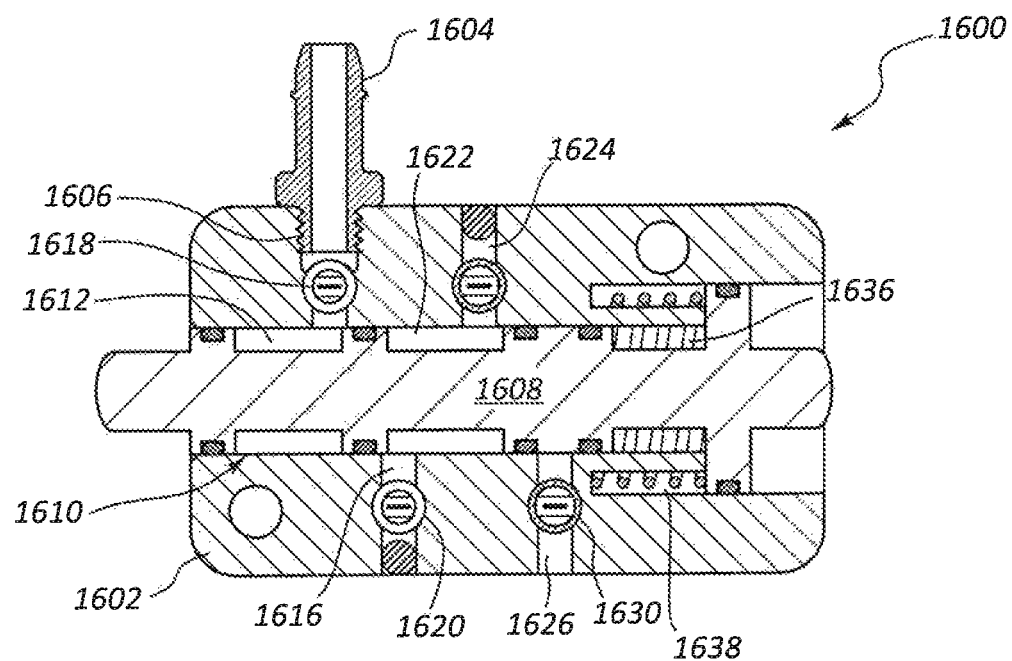
FIG. 16B is a cross-sectional view of the switch shown in FIG. 15 taken along cross-section indicators 16A-16A, the switch being arranged in a series mode.
Figure 16C:
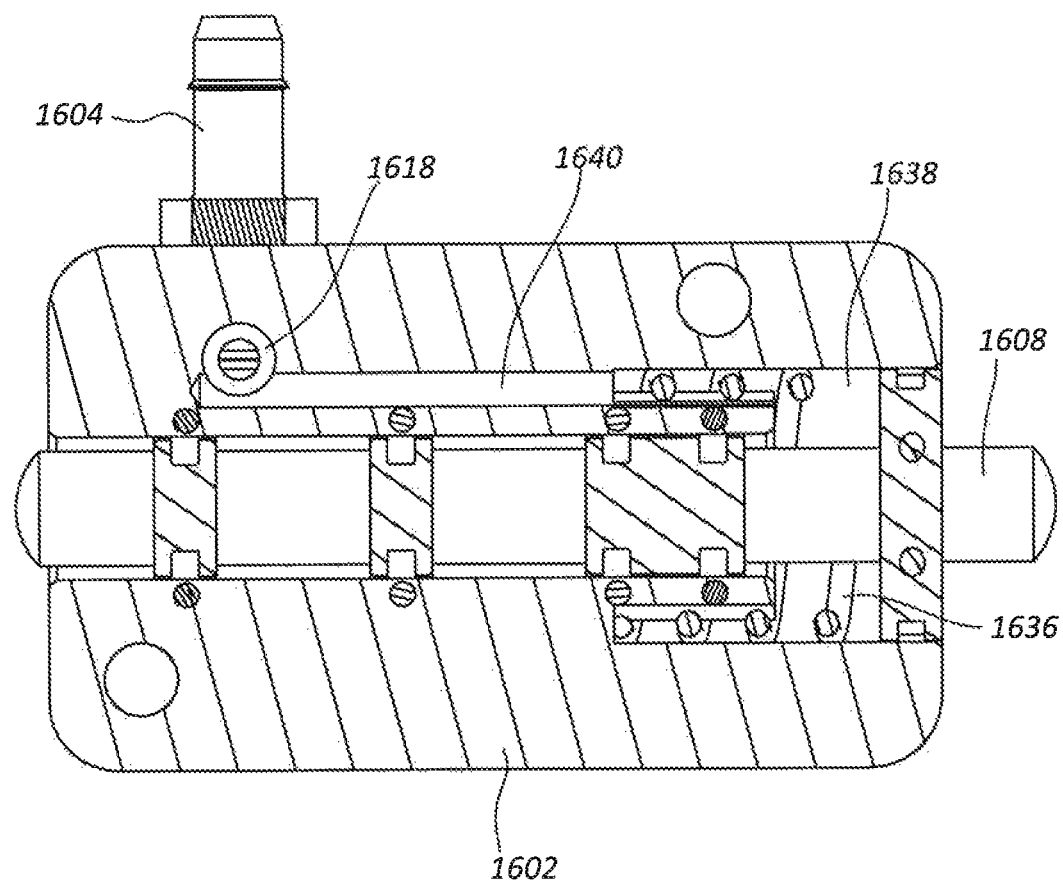
FIG. 16C is a cross-sectional side view of the switch shown in FIG. 15 taken along cross-section indicators 16C-16C, the switch being arranged in a series mode.

FIG. 15 is a side view of the switch 1302. FIGS. 16A and 16B are cross-sectional views of the switch 1302 taken through section lines 16A-16A in FIG. 15, and FIG. 16C is a cross-sectional view of the switch 1302 taken through section lines 16C-16C in FIG. 15.

FIG. 16A is a cross-sectional view of the switch 1302 in parallel mode. The switch 1302 may have an automatic function that changes the position of a spool 1608 in the switch 1302 between the position shown in FIG. 16A and the position shown in FIG. 16B. The switch 1302 may include a switch housing 1602. The switch housing 1602 may comprise a series of openings, apertures, and valves. A fluid connector 1604 may be coupled to an opening 1606 in the switch housing 1602. The fluid connector 1604 may provide a connection point to fluidly couple the switch 1302 to an evacuation volume. A spool 1608 may be situated in an opening 1610 of the switch housing 1602.

The spool 1608 may comprise a series of grooves on its outer diameter surface. The series of grooves may incorporate fluid passages enabling air flow between an evacuation volume and a vacuum pump. For example a space between the spool 1608 and the opening 1610 may form a central intake passage 1612. The central intake passage 1612 may be fluidly coupled to a first intake passage 1614 and a second intake passage 1616. The first intake passage 1614 may be fluidly coupled to a first chamber of a vacuum pump (e.g., first chamber 208, 336 as shown in FIGS. 2 and 3C) and second intake passage 1616 may be fluidly coupled to a second chamber (e.g., second chamber 210, 338 as shown in FIGS. 2 and 3C). The first intake passage 1614 and the second intake passage 1616 may include a first intake valve 1618 and a second intake valve 1620, respectively. Thus, air passing into the central intake passage 1612 may be simultaneously provided to both intake valves 1618, 1620 when the spool 1608 is in the position shown in FIG. 16A. Thus, the first and second chambers may be filled directly from the evacuation volume as is done in a parallel pump.

A second rectangular groove in the spool 1608 and the inner wall of the opening 1610 around it may comprise a central exhaust passage 1622. The central exhaust passage 1622 may be coupled to a first exhaust passage 1624 and a second exhaust passage 1626. The first exhaust passage 1624 and second exhaust passage 1626 may be fluidly coupled to a first chamber and second chamber of the vacuum pump, respectively. The first and second exhaust passages 1624, 1626 may incorporate a first and second exhaust valve 1628, 1630, respectively. Thus, air from the first and second chambers may be simultaneously vented through the second exhaust passage 1626 via the exhaust valves 1628, 1630.

When the spool 1608 is in the position shown in FIG. 16B, air may be provided to the first chamber of the pump via the first intake passage 1614 and the first intake valve 1618. The second intake valve 1620 is cut off from the central intake passage 1612 due to the shifted position of the spool 1608. Instead, the second intake valve 1620 receives air from the central exhaust passage 1622 that links the first exhaust valve 1628 (which is connected to the first chamber of the pump) to the second intake valve 1620. Air may then exhaust from the second chamber of the pump via the second exhaust valve 1630 and second exhaust passage 1626. Accordingly, the configuration shown in FIG. 16B illustrates the switch 1302 setting the vacuum pump to work as a series pump.

One end of the spool 1608 may accept a spring 1636 in a switch volume 1638. The switch volume 1638 may comprise a sealed volume. As shown in FIG. 16C, the switch volume 1638 may have its air pressure synchronized with the pressure in the evacuation volume via a spring passage 1640. The spring passage 1640 is connected to the first intake passage 1614 which is also in fluid communication with the first intake valve 1618. The pressure in the switch volume 1638 may control a position of the spool 1608. For example, the spool may be in the first position shown in FIG. 16A. When a sufficient vacuum condition is achieved in the evacuation volume (and accordingly also in the switch volume 1638), the spring 1636 may compress, as shown in FIGS. 16B and 16C, due to the pressure dropping in the spring passage 1640 and switch volume 1638. The spring 1636 may automatically compress as adequate vacuum is achieved, thereby causing the spool 1608 to move from the parallel mode of FIG. 16A to the series mode of FIG. 16B.

As mentioned previously herein, the parallel mode of the vacuum pump reduces pressure more quickly than the series mode by more quickly evacuating the evacuation volume. However, the series mode of the pump can produce a lower pressure than the parallel mode, and a lower pressure may provide a stronger connection between the prosthetic device and a residual limb. Thus, it is desirable to use parallel mode to reduce pressure quickly and then switch to series mode to deepen and strengthen the vacuum after a certain vacuum condition is reached using parallel mode. The user may not wish to have to switch manually between the two modes. The automatic switch 1700 may remove ambiguity in when to switch the pump and not rely on the user remembering to manually switch the pump to achieve optimal vacuum conditions.

Figure 17A:
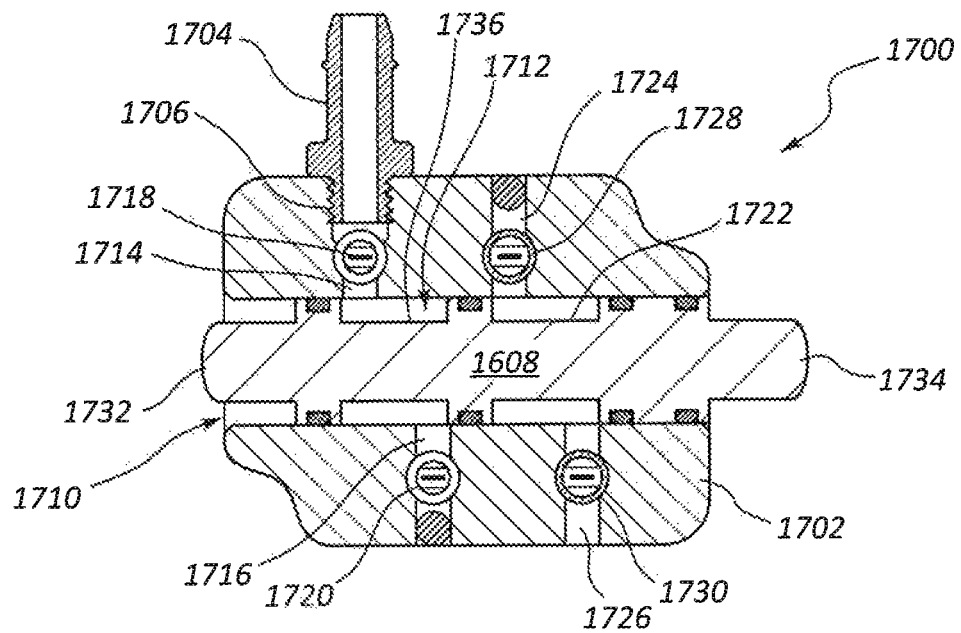
FIG. 17A is a cross-sectional view of an example switch for use in a vacuum pump in accordance with the present disclosure, the switch being arranged in a parallel mode.

FIG. 17A is a cross-sectional view of a manual switch 1700 arranged in a parallel mode. The manual switch 1700 includes a switch housing 1702. The switch housing 1702 may comprise a series of openings and apertures. A fluid connector 1704 may be coupled to an opening 1706 in the switch housing 1702. The fluid connector 1704 may provide a connection point to fluidly couple the manual switch 1700 to an evacuation volume. A spool 1708 may be situated and slidable within an opening 1712 of the switch housing 1702.

The spool 1708 may comprise a series of grooves 1722, 1736 on its outer surface. The series of grooves may, in conjunction with the inner walls of the opening 1712, form fluid passages enabling air flow between an evacuation volume and a vacuum pump. For example, a first section may act as an intake passage 1736. The intake passage 1736 may be fluidly coupled to a first intake passage 1714 and a second intake passage 1716. The first intake passage 1714 may be fluidly coupled to a first chamber of a vacuum pump (e.g., first chamber 208, 336 shown in FIGS. 2 and 3C) and second intake passage 1716 may be fluidly coupled to a second chamber of the vacuum pump (e.g., second chamber 210, 338 as shown in FIGS. 2 and 3C). The first intake passage 1714 and the second intake passage 1716 may include a first intake valve 1718 and a second intake valve 1720, respectively. Thus, the intake passage 1736 may simultaneously provide air to the first and second chambers of a vacuum pump from the fluid connector 1704.

A second groove in the spool 1708 may, in conjunction with the inner walls of the opening 1712, comprise an evacuation exhaust passage 1722. The evacuation exhaust passage 1722 may couple to a first exhaust passage 1724 and a second exhaust passage 1726. The first exhaust passage 1724 and second exhaust passage 1726 may be fluidly coupled to a first chamber and second chamber of the vacuum pump, respectively. The first and second exhaust passages 1724, 1726 may incorporate a first and second exhaust valve 1728, 1730, respectively. Thus, the evacuation exhaust passage 1722 may simultaneously receive exhaust air from the first and second chambers of the vacuum pump and allow the air to exit through the second exhaust passage 1726.

Each end of the spool 1708 may include a button, stem, or other control member. For example, a first side of the spool 1708 may incorporate a first button 1732 and the second side of the spool 1708 may incorporate a second button 1734. The buttons 1732, 1734 may enable user to engage and longitudinally slide the spool 1708 relative to the opening 1712 between a parallel position (as shown in FIG. 17A) and a series position (as shown in FIG. 17B).

Figure 17B:
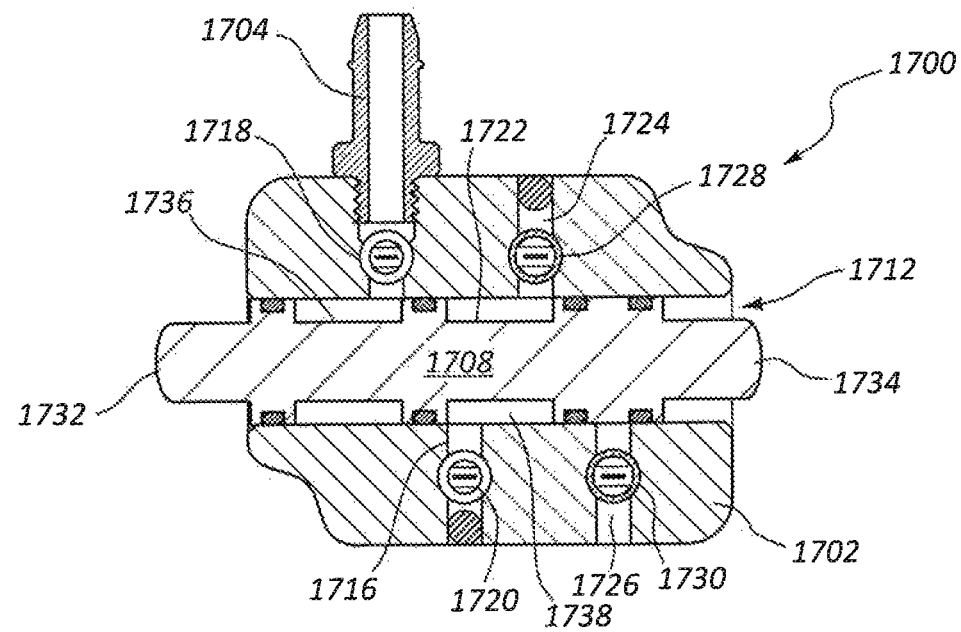
FIG. 17B is a cross-sectional view of the switch shown in FIG. 17A arranged in a series mode.

In FIG. 17B, the spool 1708 is arranged in a series mode. For example, the spool 1708 is positioned such that the intake passage 1736 may receive air from the fluid connector 1704 and provide air into one of the chambers of the vacuum pump via first intake valve 1718. Air cannot pass directly from the fluid connector 1704 into the second intake valve 1720. However, the exhaust passage 1722 is positioned relative to the second intake valve 1720 and the first exhaust valve 1728 so that air from the first chamber (via the first exhaust valve 1728) may be provided into the second chamber (via the second intake valve 1720). Air in the second chamber may then exhaust via the second exhaust valve 1730. Accordingly, the manual switch 1700 causes the pump (e.g., pump 1300) to operate as a parallel vacuum pump with the spool 1708 in the position of FIG. 17A and to operate as a series vacuum pump with the spool 1708 in the position of FIG. 17B.

As explained above, a user may switch the vacuum pump between the parallel and series modes during use of a prosthetic device to reach a certain vacuum condition quickly and then to deepen that vacuum. The manual switch 1700 of FIGS. 17A-17B allows the user to manually decide when to change from parallel mode to series mode. The two modes may provide a user with greater control over the vacuum condition in the prosthetic device and may therefore enhance its comfort and customizability.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. A vacuum pump for a prosthetic device, comprising:
a housing having an inner wall;
a piston having an outer diameter and being positioned within the housing;
a shaft having an inner surface and being positioned between the inner wall of the housing and the outer diameter of the piston;
a first evacuation chamber positioned between a top surface of the piston and the inner surface of the shaft, the first evacuation chamber having a variable volume as the shaft moves axially relative to the piston and the housing, the first evacuation chamber being fluidly connectable to a socket of the prosthetic device through a first valve and fluidly connected to atmosphere through a second valve;
a second evacuation chamber positioned between a bottom surface of the piston and the inner surface of the shaft, the second evacuation chamber having a variable volume as the shaft moves axially relative to the piston and the housing, the second evacuation chamber being fluidly connectable to the socket through a third valve and fluidly connected to atmosphere through a fourth valve.

2. The vacuum pump of claim 1, wherein the first valve and third valve are independently fluidly connectable to an evacuation volume of the socket.

3. The vacuum pump of claim 2, wherein the evacuation volume decreases as the vacuum pump operates causing a vacuum condition in the evacuation volume.

4. The vacuum pump of claim 1, wherein the shaft is axially movable to compress a volume of the first evacuation chamber while expanding a volume of the second evacuation chamber and vice versa.

5. The vacuum pump of claim 1, wherein compressing a volume of the first evacuation chamber causes air to exhaust via the second valve into atmosphere.

6. The vacuum pump of claim 1, wherein the piston is an assembly comprising:
a first piece of the piston, the first piece of the piston being substantially cylindrically shaped;
a second piece of the piston, the second piece of the piston having a torus shape.

7. The vacuum pump of claim 1, wherein the piston incorporates a series of fluid channels configured to fluidly connect the first evacuation chamber and the second evacuation chamber to the socket.

8. The vacuum pump of claim 1, further comprising:
a compressible seal positioned around an outer diameter of the piston, wherein the compressible seal fluidly separates the first evacuation chamber from the second evacuation chamber while enabling the shaft to move axially relative to the piston.

9. The vacuum pump of claim 1, wherein the valves are one-way valves allowing fluid flow in a single direction.

10. The vacuum pump of claim 1, further comprising a prosthetic leg, the prosthetic leg comprising a prosthetic foot and a socket, the socket being configured to accept a residual limb, the vacuum pump being configured to evacuate fluid from the socket.

11. A vacuum pump for a prosthetic device, comprising:
a housing having an inner wall;
a piston having an outer diameter and being positioned within and fixed relative to the housing;
a shaft having an inner surface and being positioned between the inner wall of the housing and the outer diameter of the piston;
a first evacuation chamber positioned between a top surface of the piston and the inner surface of the shaft, the first evacuation chamber having a variable volume as the shaft moves axially relative to the piston and the housing, the upper fluid chamber being fluidly connected to a first pair of one-way valves;
a second evacuation chamber positioned between a bottom surface of the piston and the inner surface of the shaft, the second evacuation chamber having a variable volume as the shaft moves axially relative to the piston and the housing, the lower fluid chamber being fluidly connected to a second pair of one-way valves.

12. The vacuum pump of claim 11, wherein at least a first valve of the first and second pair of one-way valves is configured to fluidly connect to a socket of the prosthetic device and wherein at least a second valve of the first and second pair of one-way valves is fluidly connected to atmosphere.

13. The vacuum pump of claim 11, wherein compressing a volume of the first evacuation chamber causes air to exhaust via the one of the first pair of one-way valves into atmosphere.

14. The vacuum pump of claim 11, further comprising:
a compressible seal positioned around an outer diameter of the piston, wherein the compressible seal fluidly separates the first evacuation chamber from the second evacuation chamber while enabling the shaft to move axially relative to the piston.

15. A vacuum pump for a prosthetic device, the vacuum pump comprising:
a housing having an inner wall;
a piston having an outer diameter, a top surface, and a bottom surface, the piston being held stationary relative to the housing;
a shaft having an inner surface and being positioned between the inner wall of the housing and the outer diameter of the piston;
a first evacuation chamber positioned between the top surface of the piston and the inner surface of the shaft, the first evacuation chamber having a variable volume as the shaft moves axially in relation to the piston and the housing, the first evacuation chamber being in fluid communication with a first valve and a second valve;
a second evacuation chamber positioned between the bottom surface of the piston and the inner surface of the shaft, the second evacuation chamber having a variable volume as the shaft moves axially in relation to the piston and the housing, the second evacuation chamber being in fluid communication with a third valve and a fourth valve;
a switch configured to control the operation of the vacuum pump between a parallel vacuum pump configuration in which the upper and lower fluid chambers are separately fluidly connected to a socket of the prosthetic device and a series vacuum pump configuration in which the upper and lower fluid chambers are fluidly connected in series with each other and the socket;
wherein at least one of the first and third valves is configured to fluidly connect to the socket and at least one of the second and forth valve is fluidly connected to atmosphere.

16. The vacuum pump of claim 15, wherein in the parallel vacuum pump configuration, the first and third valves are both configured to fluidly connect to the socket and the second and fourth valves are fluidly connected to atmosphere, and wherein in the series vacuum pump configuration, the first valve is configured to fluidly connect to the socket, the second valve is fluidly connected to the second evacuation chamber, the third valve is fluidly connected to the second evacuation fluid chamber, and the fourth valve is fluidly connected to atmosphere.

17. A vacuum pump for a prosthetic device, comprising:
a housing having an inner wall;
a piston having an outer diameter and being positioned within the housing;
a shaft having an inner surface and being positioned between the inner wall of the housing and the outer diameter of the piston;
a first evacuation chamber positioned between a top surface of the piston and the inner surface of the shaft, the first evacuation chamber having a variable volume as the shaft moves axially in relation to the piston and the housing, the first evacuation chamber being fluidly connectable to a socket of the prosthetic device through a first valve and fluidly connected to atmosphere through a second valve;
a second evacuation chamber positioned between a bottom surface of the piston and the inner surface of the shaft, the second evacuation chamber having a variable volume as the shaft moves axially in relation to the piston and the housing, the second evacuation chamber being fluidly connectable to the socket through a third valve and fluidly connected to atmosphere through a fourth valve;
wherein the piston incorporates a series of fluid channels configured to fluidly connect the first evacuation chamber and the second evacuation chamber to the socket.

18. The vacuum pump of claim 17, wherein the first valve and third valve are independently fluidly connectable to an evacuation volume of the socket.

19. The vacuum pump of claim 18, wherein the evacuation volume decreases as the vacuum pump operates causing a vacuum condition in the evacuation volume.

20. The vacuum pump of claim 17 wherein the shaft is axially movable to compress a volume of the first evacuation chamber while expanding a volume of the second evacuation chamber and vice versa.

21. The vacuum pump of claim 17, wherein compressing a volume of the first evacuation chamber causes air to exhaust via the second valve into atmosphere.

22. The vacuum pump of claim 17, wherein the piston is an assembly comprising:
   a first piece of the piston, the first piece of the piston being substantially cylindrically shaped;
   a second piece of the piston, the second piece of the piston having a torus shape.

* * * * *